(12) United States Patent
Ikeda et al.

(10) Patent No.: US 10,904,437 B2
(45) Date of Patent: Jan. 26, 2021

(54) CONTROL APPARATUS AND CONTROL METHOD

(71) Applicant: SONY CORPORATION, Tokyo (JP)

(72) Inventors: Kenji Ikeda, Kanagawa (JP); Hisakazu Shiraki, Kanagawa (JP); Daisuke Tsuru, Chiba (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/491,714

(22) PCT Filed: Feb. 6, 2018

(86) PCT No.: PCT/JP2018/004051
§ 371 (c)(1),
(2) Date: Sep. 6, 2019

(87) PCT Pub. No.: WO2018/168261
PCT Pub. Date: Sep. 20, 2018

(65) Prior Publication Data
US 2020/0084379 A1     Mar. 12, 2020

(30) Foreign Application Priority Data
Mar. 16, 2017   (JP) ................................ 2017-051183

(51) Int. Cl.
*H04N 5/232*    (2006.01)
*A61B 1/00*     (2006.01)
(Continued)

(52) U.S. Cl.
CPC ..... *H04N 5/23267* (2013.01); *A61B 1/00009* (2013.01); *A61B 1/00188* (2013.01);
(Continued)

(58) Field of Classification Search
CPC . A61B 1/045; A61B 1/00009; A61B 1/00078; A61B 1/00174; A61B 1/3132;
(Continued)

(56) References Cited

U.S. PATENT DOCUMENTS

2008/0180385 A1* 7/2008 Yoshida ............... G09G 3/3413
345/102
2010/0092151 A1* 4/2010 Miyakoshi ......... H04N 21/4325
386/343
(Continued)

FOREIGN PATENT DOCUMENTS

CN   105850120 A   8/2016
EP   3070941 A1    9/2016
(Continued)

OTHER PUBLICATIONS

Munzer et al., "Content-based processing and analysis of endoscopic images and Videos"; Springerlink.com;Jan. 11, 2017; DOI 10.1007/s 11042-016-4219-z (Year: 2017).*
(Continued)

*Primary Examiner* — Dramos Kalapodas
(74) *Attorney, Agent, or Firm* — Chip Law Group

(57) ABSTRACT

There is provided a control apparatus that includes an estimating section calculating motion of an entire image on the basis of an image signal corresponding to an optical image of a living organism input from an imaging section of a medical observation apparatus, to estimate blurring of the entire image according to a result of the calculation, and a control section controlling an operation related to correction of the blurring of the entire image by controlling a coefficient for controlling an amount of correction of the blurring on the basis of a zoom magnification of the imaging section such that a degree of correction of the blurring increases consistently with the zoom magnification.

9 Claims, 31 Drawing Sheets

(51) Int. Cl.
  *A61B 1/045* (2006.01)
  *A61B 1/313* (2006.01)
  *A61B 90/00* (2016.01)
  *A61B 90/50* (2016.01)
  *A61B 18/00* (2006.01)
  *H04N 5/225* (2006.01)

(52) U.S. Cl.
  CPC ............ *A61B 1/045* (2013.01); *A61B 1/3132* (2013.01); *H04N 5/23254* (2013.01); *A61B 18/00* (2013.01); *A61B 90/361* (2016.02); *A61B 90/50* (2016.02); *H04N 2005/2255* (2013.01)

(58) Field of Classification Search
  CPC .......... A61B 1/00154; A61B 17/00234; A61B 17/3432; A61B 34/75; A61B 1/00188; A61B 1/04; H04N 5/23267; H04N 5/23254; H04N 5/232; H04N 5/225; G02B 12/24
  See application file for complete search history.

(56) References Cited

U.S. PATENT DOCUMENTS

| | | | |
|---|---|---|---|
| 2011/0193990 A1* | 8/2011 | Pillman | H04N 5/23245 348/229.1 |
| 2012/0071718 A1 | 3/2012 | On | |
| 2012/0092472 A1* | 4/2012 | Higuchi | A61B 1/00009 348/65 |
| 2012/0262559 A1* | 10/2012 | On | H04N 5/23267 348/65 |
| 2014/0088353 A1 | 3/2014 | Hayama | |
| 2015/0182118 A1* | 7/2015 | Bradbury | A61P 25/02 600/431 |
| 2016/0269713 A1* | 9/2016 | Kasumi | G06T 7/11 |
| 2017/0027416 A1 | 2/2017 | Hayashi | |
| 2017/0258528 A1* | 9/2017 | Bai | G02B 23/2415 |
| 2018/0316870 A1* | 11/2018 | Yoshino | A61B 1/00009 |

FOREIGN PATENT DOCUMENTS

| | | |
|---|---|---|
| EP | 3099213 A1 | 12/2016 |
| EP | 3247113 A1 | 11/2017 |
| JP | 2012-065690 A | 4/2012 |
| JP | 2012-085696 A | 5/2012 |
| JP | 2014-064657 A | 4/2014 |
| JP | 2015-096237 A | 5/2015 |
| JP | 2015-139646 A | 8/2015 |
| JP | 2016-131276 A | 7/2016 |
| WO | 2015/111263 A1 | 7/2015 |
| WO | 2015/115073 A1 | 8/2015 |
| WO | 2016/114155 A1 | 7/2016 |
| WO | 2016/158119 A1 | 10/2016 |
| WO | 2017/169139 A1 | 10/2017 |

OTHER PUBLICATIONS

International Search Report and Written Opinion of PCT Application No. PCT/JP2018/004051, dated Mar. 20, 2018, 11 pages of ISRWO.

* cited by examiner

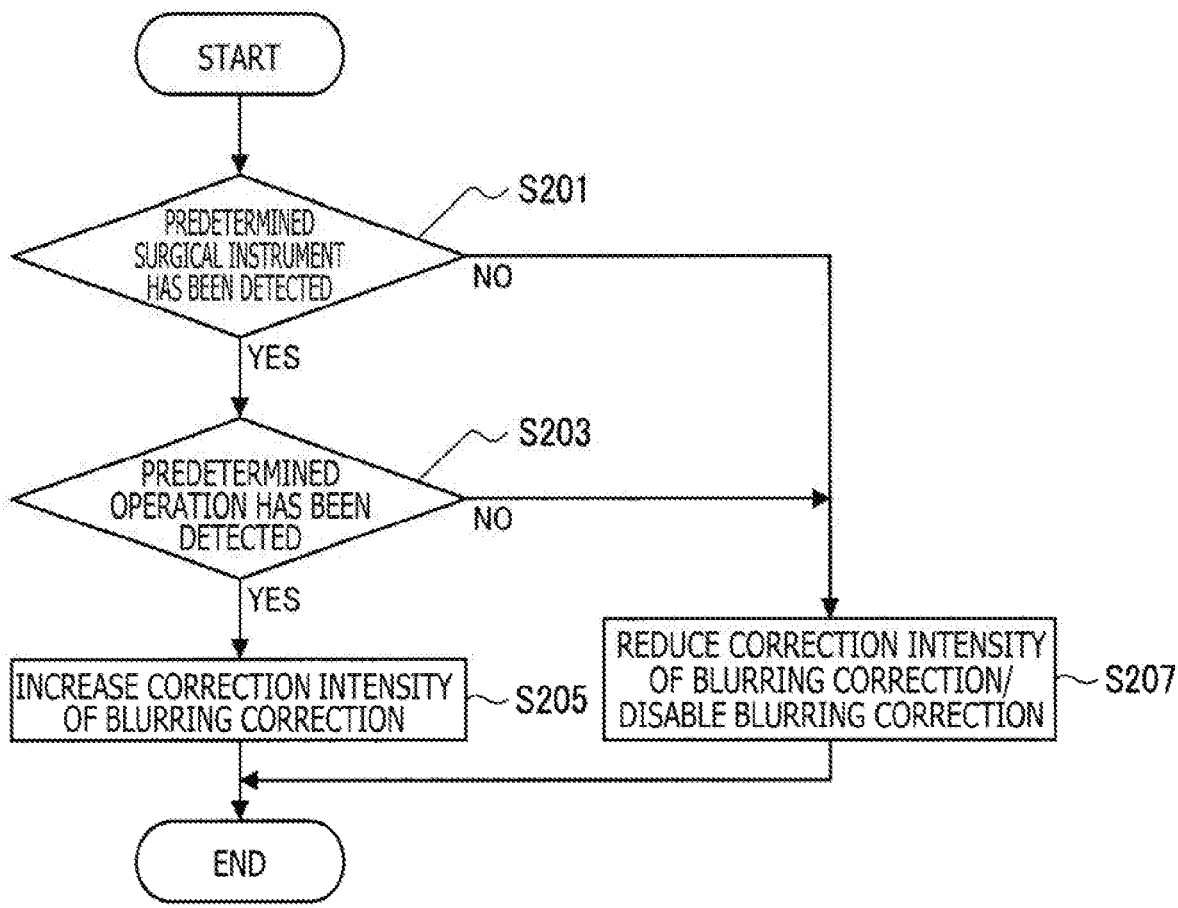

CONTROL APPARATUS AND CONTROL METHOD

CROSS REFERENCE TO RELATED APPLICATIONS

This application is a U.S. National Phase of International Patent Application No. PCT/JP2018/004051 filed on Feb. 6, 2018, which claims priority benefit of Japanese Patent Application No. JP 2017-051183 filed in the Japan Patent Office on Mar. 16, 2017. Each of the above-referenced applications is hereby incorporated herein by reference in its entirety.

TECHNICAL FIELD

The present disclosure relates to a control apparatus, a control method, and a program.

BACKGROUND ART

In recent years, with developed surgical procedures and instruments, surgery (what is called microsurgery) has frequently been performed in which various treatments are offered while a diseased site is being observed with a medical observation apparatus such as a surgical microscope or an endoscope. Additionally, such medical observation apparatuses are not limited to apparatuses enabling the diseased site to be optically observed but include apparatuses causing a display apparatus such as a monitor or a display to display, as an electronic image, an image of the diseased site captured using an imaging section (camera) or the like.

CITATION LIST

Patent Literature

[PTL 1]
Japanese Patent Laid-Open No. 2015-139646

SUMMARY

Technical Problem

Incidentally, with an endoscope apparatus, in a case where a hand or the like holding a camera head is shaken, motion of the shake is transmitted to an objective lens, and thus, image blurring may be caused by the shake of the hand or the like. Accordingly, in recent years, an endoscope apparatus has been proposed to which a technique for correcting the image blurring caused by the shake of the hand or the like is applied. For example, PTL 1 discloses an example of the technique for correcting the image blurring caused by the shake of the hand or the like in the endoscope apparatus.

On the other hand, observation of a living organism with a medical observation apparatus such as an endoscope involves variations in conditions, environments, and the like related to the observation, and the effect of correction of the image blurring on the visibility of an observation target (living organism or the like) varies according to circumstances of the moment. Thus, even in a case where the image blurring is corrected under the same conditions as those in certain circumstances, the visibility of the observation target is not necessarily improved in other circumstances.

Thus, the present disclosure proposes a control apparatus, a control method, and a program that can correct the image blurring in a more suitable manner according to the circumstances related to the observation of the living organism.

Solution to Problem

According to the present disclosure, a control apparatus is provided that includes an estimating section calculating motion of an entire image on the basis of an image signal corresponding to an optical image of a living organism input from an imaging section of a medical observation apparatus, to estimate blurring of the entire image according to a result of the calculation, and a control section controlling an operation related to correction of the blurring of the entire image by controlling a coefficient for controlling an amount of correction of the blurring on the basis of a zoom magnification of the imaging section such that a degree of correction of the blurring increases consistently with the zoom magnification.

Additionally, according to the present disclosure, a control apparatus is provided that includes an estimating section calculating motion of an entire image on the basis of an image signal corresponding to an optical image of a living organism input from an imaging section of a medical observation apparatus, to estimate blurring of the entire image according to a result of the calculation, and a control section controlling an operation related to correction of the blurring of the entire image on the basis of a ratio of a region of the living organism in the image signal, the region being shielded by a subject different from the living organism.

Additionally, according to the present disclosure, a control method is provided that includes calculating, by a computer, motion of an entire image on the basis of an image signal corresponding to an optical image of a living organism input from an imaging section of a medical observation apparatus, to estimate blurring of the entire image according to a result of the calculation, and controlling, by the computer, an operation related to correction of the blurring of the entire image by controlling a coefficient for controlling an amount of correction of the blurring on the basis of a zoom magnification of the imaging section such that a degree of correction of the blurring increases consistently with the zoom magnification.

Additionally, according to the present disclosure, a control method is provided that includes calculating, by a computer, motion of an entire image on the basis of an image signal corresponding to an optical image of a living organism input from an imaging section of a medical observation apparatus, to estimate blurring of the entire image according to a result of the calculation, and controlling, by the computer, an operation related to correction of the blurring of the entire image on the basis of a ratio of a region of the living organism in the image signal, the region being shielded by a subject different from the living organism.

Additionally, according to the present disclosure, a program is provided that causes a computer to execute calculating motion of an entire image on the basis of an image signal corresponding to an optical image of a living organism input from an imaging section of a medical observation apparatus, to estimate blurring of the entire image according to a result of the calculation, and controlling an operation related to correction of the blurring of the entire image by controlling a coefficient for controlling an amount of correction of the blurring on the basis of a zoom magnification of the imaging section such that a degree of correction of the blurring increases consistently with the zoom magnification.

Additionally, according to the present disclosure, a program is provided that causes a computer to execute calculating motion of an entire image on the basis of an image signal corresponding to an optical image of a living organism input from an imaging section of a medical observation apparatus, to estimate blurring of the entire image according to a result of the calculation, and controlling an operation related to correction of the blurring of the entire image on the basis of a ratio of a region of the living organism in the image signal, the region being shielded by a subject different from the living organism.

Advantageous Effect of Invention

As described above, according to the present disclosure, a control apparatus, a control method, and a program are provided that can correct image blurring in a more suitable manner according to circumstances related to observation of a living organism.

Note that the above-described effect is not restrictive and that, in addition to or instead of the above-described effect, any of effects disclosed herein or other effects understood from the specification may be exerted.

BRIEF DESCRIPTION OF DRAWINGS

FIG. 22 is a descriptive diagram illustrating an example of the control related to the correction of image blurring performed by the control apparatus according to Example 9.

FIG. 23 is a descriptive diagram illustrating an example of the control related to the correction of image blurring performed by the control apparatus according to Example 9.

DESCRIPTION OF EMBODIMENT

A preferred embodiment of the present disclosure will be described below in detail with reference to the accompanying drawings. Note that, in the specification and the drawings, components having substantially the same functional configurations are denoted by the same reference signs and that duplicate description of these components is omitted.

Note that the description is in the following order.
1. Example of Configuration of Medical Observation System
2. Technical Features
2.1 Basic Configuration
2.2 Processing
2.3 Examples
3. Applied Example
4. Example of Hardware Configuration
5. Conclusion

1. Example of Configuration of Medical Observation System

First, with reference to FIG. 1 and FIG. 2, an example of a general configuration of a medical observation system according to the embodiment of the present disclosure will be described.

Figure 1:
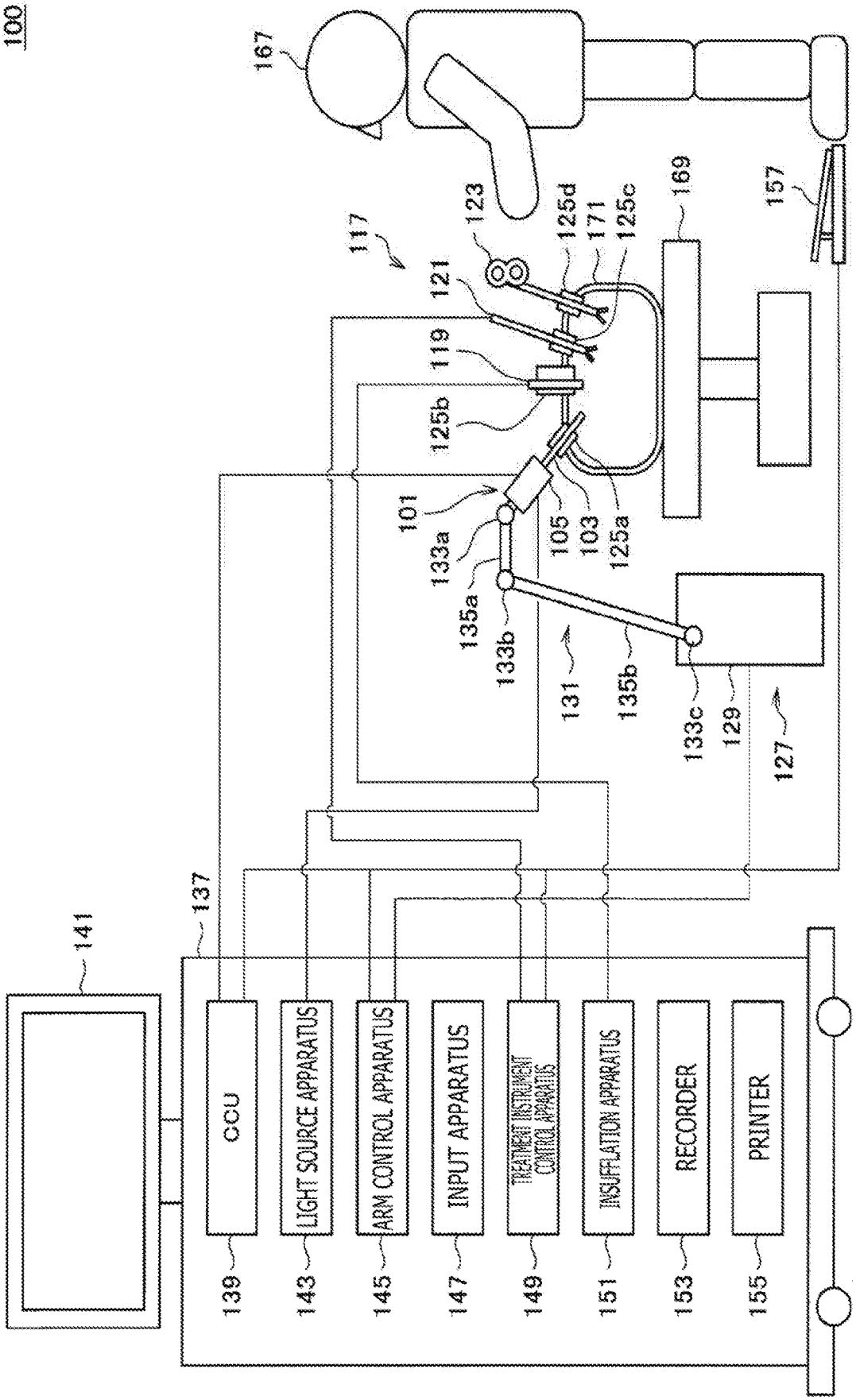
FIG. 1 is a diagram illustrating an example of a general configuration of an endoscopic imaging system according to an embodiment of the present disclosure.

For example, FIG. 1 is a diagram illustrating an example of a general configuration of a medical observation system to which a technique according to the present disclosure may be applied. FIG. 1 illustrates an example in which the medical observation system is configured as what is called an endoscopic surgery system. FIG. 1 illustrates that an operator (surgeon) 167 is operating on a patient 171 on a patient bed 169 using an endoscopic surgery system 100. As illustrated in FIG. 1, the endoscopic surgery system 100 includes an endoscope 101, other surgical instruments 117, a support arm apparatus 127 supporting the endoscope 101, and a cart 137 in which various apparatuses for endoscopic surgery are loaded.

Endoscopic surgery involves stabbing, into the abdominal wall, a plurality of tubular opening instruments referred to as trocars 125*a* to 125*d*, instead of incising the abdominal wall for laparotomy. Then, a lens barrel 103 of the endoscope 101 and the other surgical instruments 117 are inserted into the body cavity of the patient 171 through the trocars 125*a* to 125*d*. In the illustrated example, as the other surgical instrument 117, an insufflation tube 119, an energy treatment instrument 121, and forceps 123 are inserted into the body cavity of the patient 171. Additionally, the energy treatment instrument 121 is a treatment instrument used for incision and exfoliation of tissues, sealing of blood vessels, and the like using a high-frequency current or ultrasonic vibration. However, the surgical instruments 117 are only examples, and as the surgical instruments 117, various surgical instruments generally used in endoscopic surgeries may be used, for example, tweezers and a retractor.

An image of an affected site in the body cavity of the patient 171 captured using the endoscope 101 is displayed on a display apparatus 141. While viewing, in real time, the image of the affected site displayed on the display apparatus 141, the operator 167 offers treatment such as excision of a diseased site using the energy treatment instrument 121 and the forceps 123. Note that, although not illustrated, the insufflation tube 119, the energy treatment instrument 121, and the forceps 123 are supported by the operator 167, an assistant, or the like during surgery.

(Support Arm Apparatus)

The support arm apparatus 127 includes an arm section 131 extending from a base section 129. In the illustrated example, the arm section 131 includes joint sections 133*a*, 133*b*, and 133*c* and links 135*a* and 135*b*, and driven under the control of an arm control apparatus 145. The arm section 131 supports the endoscope 101 and controls the position and posture of the endoscope 101. This allows the position of the endoscope 101 to be stably fixed.

(Endoscope)

The endoscope 101 includes the lens barrel 103 including a region having a predetermined length from a distal end of the lens barrel 103 and inserted into the body cavity of the patient 171, and a camera head 105 connected to a proximal end of the lens barrel 103. In the illustrated example, the endoscope 101 is illustrated that is configured as what is called a hard mirror including a hard lens barrel 103. However, the endoscope 101 may be configured as what is called a soft mirror including a soft lens barrel 103.

The lens barrel 103 includes an opening formed at the distal end of the lens barrel 103 and in which an objective lens is fitted. A light source apparatus 143 is connected to the endoscope 101, and light generated by the light source apparatus 143 is guided to the distal end of the lens barrel by a light guide extending inside the lens barrel 103. The light is then irradiated via the objective lens toward an observation target (in other words, an imaging target) in the body cavity of the patient 171. Note that the endoscope 101 may be a forward-viewing endoscope, a forward-oblique viewing endoscope, or a side-viewing endoscope.

The camera head 105 is internally provided with an optical system and an imaging element, and reflected light (observation light) from the observation target is concentrated on the imaging element by the optical system. The observation light is photoelectrically converted by the imaging element to generate an electric signal corresponding to the observation light, that is, an image signal corresponding to the observation image. The image signal is transmitted to a camera control unit (CCU) 139 as RAW data. Note that the camera head 105 has a function to adjust magnification and a focal length by appropriately driving the optical system of the camera head 105.

Note that the camera head 105 may be provided with a plurality of imaging elements in order to support stereoscopic viewing (3D display) or the like. In this case, a plurality of relay optical systems are provided in the lens barrel 103 to guide the observation light to each of the plurality of imaging elements.

(Various Apparatuses Loaded in Cart)

The CCU 139 includes a CPU (Central Processing Unit), a GPU (Graphics Processing Unit), and the like to integrally control operations of the endoscope 101 and the display apparatus 141. Specifically, the CCU 139 executes various types of image processing, for example, development processing (demosaic processing), on an image signal received from the camera head 105 in order to display an image based on the image signal. The CCU 139 provides, to the display apparatus 141, the image signal on which the image processing has been executed. Additionally, the CCU 139 transmits a control signal to the camera head 105 to control driving of the camera head 105. The control signal may include information related to imaging conditions such as the magnification and the focal length.

The display apparatus 141 displays, under the control of the CCU 139, an image based on the image signal and subjected to the image processing by the CCU 139. In a case where the endoscope 101 supports image capturing at high resolution, for example, 4K (the number of horizontal pixels 3840×the number of vertical pixels 2160) or 8K (the number of horizontal pixels 7680×the number of vertical pixels 4320) and/or supports 3D display, the display apparatus 141 used can correspondingly provide high-resolution display and/or 3D display. In a case where the endoscope 101 supports image capturing at high resolution such as 4K or 8K, use of the display apparatus 141 having a size of 55 inches or more provides a stronger sense of immersion. Additionally, a plurality of the display apparatuses 141 varying in resolution and size may be provided according to an intended use.

The light source apparatus 143 includes a light source such as an LED (light emitting diode), and supplies irradiation light to the endoscope 101 when an image of the affected site is captured.

The arm control apparatus 145 includes a processor such as a CPU, and operates in accordance with a predetermined program to control driving of the arm section 131 of the support arm apparatus 127 in accordance with a predetermined control scheme.

The input apparatus 147 is an input interface for the endoscopic surgery system 100. A user can input various types of information and instructions to the endoscopic surgery system 100 via the input apparatus 147. For example, the user inputs, via the input apparatus 147, various types of information related to the surgery such as physical information regarding the patient and information regarding an operative procedure. Additionally, for example, the user inputs, via the input apparatus 147, an instruction to drive the arm section 131, an instruction to change the imaging conditions for the endoscope 101 (type of irradiation light, magnification, focal length, and the like), an instruction to drive the energy treatment instrument 121, and the like.

The type of the input apparatus 147 is not limited, and the input apparatus 147 may any of various well-known input apparatuses. Applicable examples of the input apparatus 147 include a mouse, a keyboard, a touch panel, a switch, a foot switch 157, and/or a lever. In a configuration in which a touch panel is used as the input apparatus 147, the touch panel may be provided on a display surface of the display apparatus 141.

Alternatively, the input apparatus 147 is a device worn by the user, such as an eyeglass-type wearable device or an HMD (Head Mounted Display), and various inputs are provided according to gestures or the line of sight of the user detected by these devices. Additionally, the input apparatus 147 includes a camera that can detect motion of the user, and various inputs are provided according to gestures or the line of sight of the user detected in a video captured by the camera. Furthermore, the input apparatus 147 includes a microphone capable of collecting voice of the user, and various aural inputs are provided via the microphone. Accordingly, the input apparatus 147 is configured to enable various types of information to be input in a non-contact manner. This particularly enables a user belonging to a clean field (for example, the operator 167) to operate, in a non-contact manner, equipment belonging to an unclean field. Additionally, the user can operate the equipment without a need to release a hand of the user from a surgical instrument held by the user, thus improving usability for the user.

A treatment instrument control apparatus 149 controls driving of the energy treatment instrument 121 for cauterizing or incising tissues, sealing blood vessels, and the like. An insufflation apparatus 151 feeds a gas into the body cavity of the patient 171 via the insufflation tube 119 to inflate the body cavity for the purpose of allowing the endoscope 101 to provide an appropriate field of view and providing an appropriate workspace for the operator. A recorder 153 is an apparatus that can record various types of information related to the surgery. A printer 155 is an apparatus that can print various types of information related to the surgery in any of various formats such as a text, an image, or a graph.

Particularly characteristic configurations of the endoscopic surgery system 100 will be described below in further detail.

(Support Arm Apparatus)

The support arm apparatus 127 includes a base section 129 corresponding to a base, and the arm section 131 extending from the base section 129. In the illustrated example, the arm section 131 includes the plurality of joint sections 133a, 133b, and 133c and the plurality of links 135a and 135b coupled by the joint section 133b. However, FIG. 1 illustrates the configuration of the arm section 131 in a simplified manner for simplification. In actuality, the following may be appropriately set so as to provide the arm section 131 with a desired degree of freedom: the shapes, numbers, and arrangements of the joint sections 133a to 133c and the links 135a and 135b, the directions of rotation axes of the joint sections 133a to 133c, and the like. For example, the arm section 131 may suitably be configured to have six or more degrees of freedom. Thus, the endoscope 101 can be freely moved within a movable range of the arm section 131, enabling the lens barrel 103 of the endoscope 101 to be inserted into the body cavity of the patient 171 from a desired direction.

The joint sections 133a to 133c are provided with actuators and configured to be rotatable around predetermined rotation axes under driving of the actuators. The driving of the actuators is controlled by the arm control apparatus 145 to control the rotation angle of each of the joint sections 133a to 133c, thus controlling driving of the arm section 131. Accordingly, control of the position and posture of the endoscope 101 may be implemented. In this case, the arm control apparatus 145 can control the driving of the arm section 131 using various well-known control schemes such as force control and position control.

For example, the operator 167 may provide an appropriate operation input via the input apparatus 147 (including the foot switch 157) to cause the arm control apparatus 145 to appropriately control the driving of the arm section 131 in accordance with the operation input, thus controlling the position and posture of the endoscope 101. The control allows the endoscope 101 at the distal end of the arm section 131 to be moved from an optional position to another optional position and then fixedly supported at a position resulting from the movement. Note that the arm section 131 may be operated on the basis of what is called a master slave scheme. In this case, the arm section 131 may be remotely operated by the user via the input apparatus 147 installed at a distance from the operating room.

Additionally, in a case where force control is applied, what is called power assist control may be performed in which the arm control apparatus 145 receives an external force from the user and drives the actuators for the joint sections 133a to 133c to smoothly move the arm section 131 in conjunction with the external force. Thus, when directly contacting and moving the arm section 131, the user can move the arm section 131 by a relatively weak force. Accordingly, the endoscope 101 can be intuitively moved by easier operation, thus improving usability for the user.

Here, in general, in endoscopic surgeries, the endoscope 101 is supported by a surgeon referred to as a scopist. In contrast, the use of the support arm apparatus 127 enables the position of the endoscope 101 to be more reliably fixed without any manual operation. Accordingly, an image of the affected site can be stably obtained, enabling the surgery to be smoothly performed.

Note that the arm control apparatus 145 need not necessarily be provided in the cart 137. Additionally, the arm control apparatus 145 need not necessarily be a single apparatus. For example, the arm control apparatus 145 may be provided in each of the joint sections 133a to 133c of the arm section 131 of the support arm apparatus 127, and a plurality of the arm control apparatuses 145 may cooperate with one another in implementing driving control of the arm section 131.

(Light Source Apparatus)

The light source apparatus 143 supplies the endoscope 101 with irradiation light for imaging of the affected site. The light source apparatus 143 includes, for example, a white light source including an LED, a laser light source, or a combination of the LED and the laser light source. In this case, in a case where the white light source includes a combination of an R laser light source, a G laser light source, and a B laser light source, an output intensity and an output timing of each color (each wavelength) can be accurately controlled, and thus, the light source apparatus 143 can adjust white balance of a captured image. Additionally, in this case, images corresponding to R, G, and B can be captured in a time-division manner by irradiating an observation target with laser light beams from the R, G, and B laser light sources in a time-division manner and controlling driving of the imaging elements of the camera head 105 in synchronism with irradiation timings. This method allows color images to be obtained with no color filter provided in each of the imaging elements.

Additionally, driving of the light source apparatus 143 may be controlled so as to change the intensities of output light beams at predetermined time intervals. Driving of the imaging elements of the camera head 105 is controlled in synchronism with timings to change the intensities of the corresponding light beams to acquire images in a time-division manner and the images are synthesized. Then, what is called a high-dynamic-range image can be generated that is free from blocked up shadows and blown out highlights.

Additionally, the light source apparatus 143 may be configured to be capable of supplying light of a predetermined wavelength band enabling special light observation. In the special light observation, for example, narrow band imaging is performed in which the dependence, on wavelength, of light absorption in the body tissue is utilized to capture a high-contrast image of a predetermined tissue such as a mucous membrane surface layer blood vessel by irradiation with light of a band narrower than the band of the irradiation light for normal observation (that is, white light). Alternatively, in the special light observation, fluorescence observation may be performed in which an image is obtained using fluorescence generated by irradiation with excitation light. In the fluorescence observation, for example, the body tissue may be irradiated with excitation light, with fluorescence from the body tissue observed (autofluorescence observation), or a reagent such as indocyanine green (ICG) may be locally injected into the body tissue, which is irradiated with excitation light corresponding to the fluorescent wavelength of the reagent to obtain a fluorescent image. The light source apparatus 143 may be configured to be capable of supplying narrow band light and/or excitation light enabling such special light observation.

(Camera Head and CCU)

Figure 2:
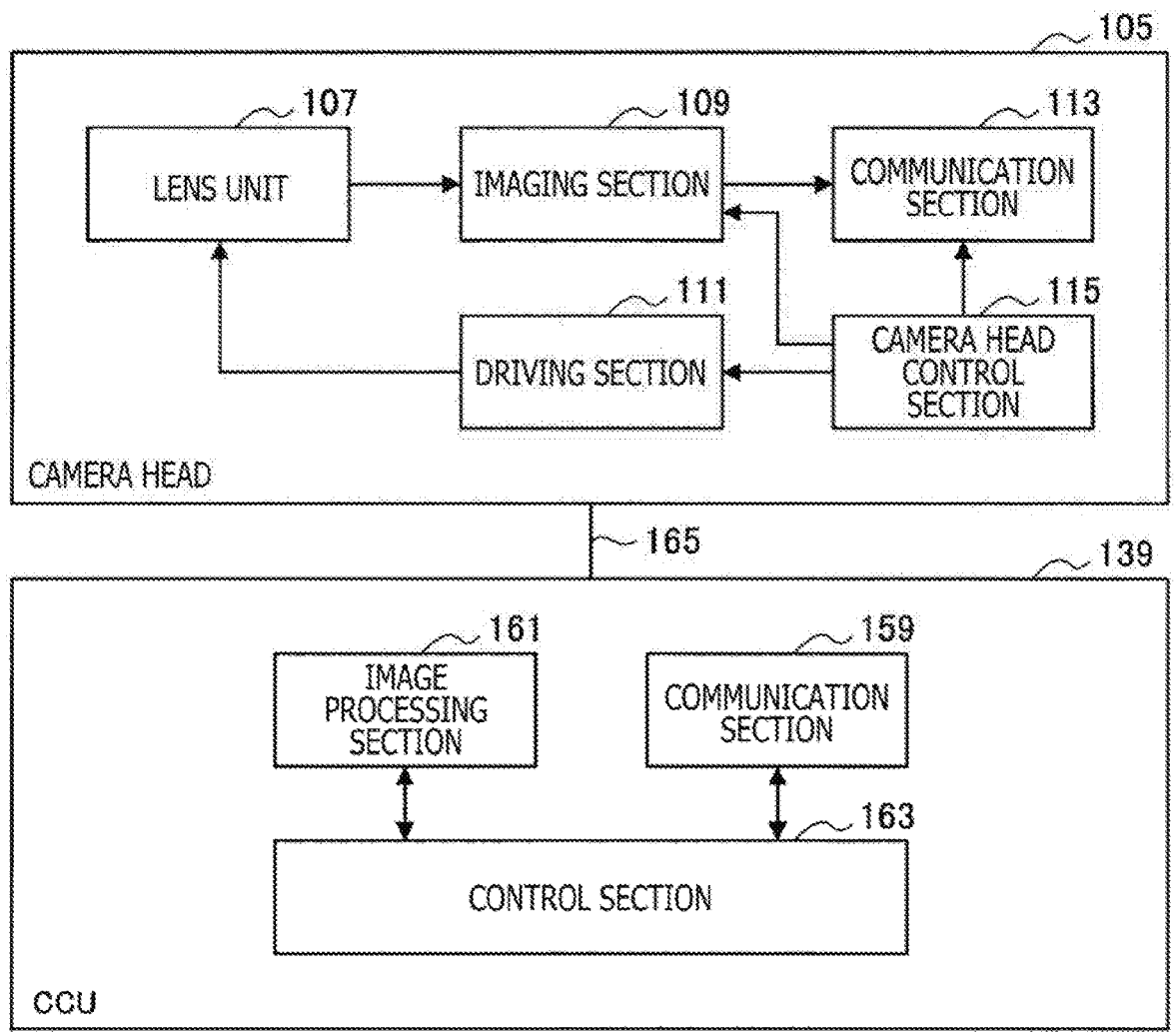
FIG. 2 is a block diagram illustrating an example of functional configurations of a camera head and a CCU illustrated in FIG. 1.

With reference to FIG. 2, functions of the camera head 105 of the endoscope 101 and the CCU 139 will be described in further detail. FIG. 2 is a block diagram illustrating an example of functional configurations of the camera head 105 and the CCU 139 illustrated in FIG. 1.

With reference to FIG. 2, the camera head 105 includes, as functions of the camera head 105, a lens unit 107, an imaging section 109, a driving section 111, a communication section 113, and a camera head control section 115. Additionally, the CCU 139 includes, as functions of the CCU 139, a communication section 159, an image processing section 161, and a control section 163. The camera head 105 and the CCU 139 are connected together with a transmission cable 165 so as to be capable of bidirectional communication.

First, the functional configuration of the camera head 105 will be described. The lens unit 107 is an optical system provided at a connection with the lens barrel 103. Observation light captured from the distal end of the lens barrel 103 is guided to the camera head 105 and enters the lens unit 107. The lens unit 107 includes a combination of a plurality of lenses including a zoom lens and a focus lens. The lens unit 107 has optical properties adjusted to concentrate observation light on light receiving surfaces of imaging elements of the imaging section 109. Additionally, a zoom lens and a focus lens are configured such that the positions of the lenses on an optical axis can be moved to adjust the magnification and focus of the captured image.

The imaging section 109 includes imaging elements and disposed succeeding the lens unit 107. The observation light having passed through the lens unit 107 is concentrated on the light receiving surfaces of the imaging elements and subjected to photoelectric conversion to generate an image signal corresponding to an observation image. The image signal generated by the imaging section 109 is provided to the communication section 113.

As the imaging elements constituting the imaging section 109, for example, CMOS (Complementary Metal Oxide Semiconductor)-type image sensors are used that have a Bayer arrangement and that can capture color images. Note that imaging elements may be used that can support, for example, capturing of images of a high resolution of 4K or more. An image of the affected site is obtained at high resolution to allow the operator 167 to understand the state of the affected site in further detail, enabling the surgery to proceed more smoothly.

Additionally, the imaging elements constituting the imaging section 109 include a pair of imaging elements intended to acquire image signals for the right eye and the left eye supporting 3D display. The 3D display enables the operator 167 to accurately understand the depth of the biological tissue in the affected site. Note that, in a case where the imaging section 109 includes multiple plates, a plurality of the lens units 107 are provided in correspondence with the respective imaging elements.

Additionally, the imaging section 109 need not necessarily be provided in the camera head 105. For example, the imaging section 109 may be provided in the lens barrel 103 located succeeding the objective lens.

The driving section 111 includes an actuator and moves the zoom lens and the focus lens of the lens unit 107 a predetermined distance along the optical axis under the control of the camera head control section 115. Accordingly, the magnification and focus of the captured image provided by the imaging section 109 may be appropriately adjusted.

The communication section 113 includes a communication apparatus configured to transmit and receive various types of information to and from the CCU 139. The communication section 113 transmits the image signal obtained from the imaging section 109, to the CCU 139 via the transmission cable 165 as RAW data. At this time, to display the captured image of the affected site with low latency, the corresponding image signal is preferably transmitted by optical communication. The reason for the use of optical communication is as follows: during the surgery, the operator 167 performs the surgery while observing the state of the diseased site in the captured image, and thus, for more safe and reliable surgery, a moving image of the affected site is required to be displayed in real time whenever possible. In a case where optical communication is performed, the communication section 113 is provided with a photoelectric converting module that converts an electric signal into an optical signal. After the image signal is converted into the optical signal by the photoelectric converting module, the optical signal is transmitted to the CCU 139 via the transmission cable 165.

Additionally, the communication section 113 receives, from the CCU 139, a control signal for controlling driving of the camera head 105. The control signal includes information related to the imaging conditions, for example, information specifying a frame rate for the captured image, information specifying the value of exposure at the time of imaging, and/or information specifying the magnification and focus of the captured image. The communication section 113 provides the received control signal to the camera head control section 115. Note that the control signal from the CCU 139 may also be transmitted by optical communication. In this case, the communication section 113 is provided with a photoelectric converting module that converts an optical signal into an electric signal. After the control signal is converted into the electric signal, the electric signal is provided to the camera head control section 115.

Note that the above-described imaging conditions such as the frame rate, the exposure value, the magnification, and the focus are automatically set by the control section 163 of the CCU 139 on the basis of the acquired image signal. In other words, what is called an AE (Auto Exposure) function, an AF (Auto Focus) function, and an AWB (Auto White Balance) function are provided in the endoscope 101.

The camera head control section 115 controls driving of the camera head 105 on the basis of the control signal received from the CCU 139 via the communication section 113. For example, the camera head control section 115 controls driving of the imaging elements of the imaging section 109 on the basis of the information specifying the frame rate for the captured image and/or the information specifying the exposure at the time of imaging. Additionally, for example, the camera head control section 115 appropriately moves the zoom lens and the focus lens of the lens unit 107 via the driving section 111 on the basis of the information specifying the magnification and focus of the captured image. The camera head control section 115 may further include a function to store information used to identify the lens barrel 103 and the camera head 105.

Note that, by disposing components such as the lens unit 107 and the imaging section 109 in a closed structure with high airtightness and high waterproofness, the camera head 105 can be made resistant to autoclave sterilization processing.

Now, the functional configuration of the CCU 139 will be described. The communication section 159 includes a communication apparatus configured to transmit and receive various types of information to and from the camera head 105. The communication section 159 receives, from the camera head 105, an image signal transmitted via the transmission cable 165. At this time, as described above, the image signal is suitably transmitted by optical communication. In this case, corresponding to the optical communication, the communication section 159 is provided with a photoelectric converting module that converts an optical signal into an electric signal. The communication section 159 provides the image processing section 161 with the image signal converted into the electric signal.

Additionally, the communication section 159 transmits, to the camera head 105, a control signal for controlling driving of the camera head 105. The control signal may also be transmitted by optical communication.

The image processing section 161 executes various types of image processing on the image signal, which is RAW data transmitted from the camera head 105. The image processing includes various types of well-known signal processing, for example, development processing, image quality improvement processing (for example, band emphasis processing, super-resolution processing, NR (Noise Reduction) processing, and/or image stabilization processing), and/or enlargement processing (electronic zoom processing). Additionally, the image processing section 161 executes a detection processing on the image signal in order to perform AE, AF, and AWB.

The image processing section 161 includes a processor such as a CPU or a GPU, and the processor may operate in accordance with a predetermined program to execute the above-described image processing or detection processing. Note that, in a case where the image processing section 161 includes a plurality of GPUs, the image processing section 161 appropriately divides the information related to the image signal, and the plurality of GPUs execute image processing in parallel.

The control section 163 performs various types of control related to capturing of an image of the affected site by the endoscope 101 and display of the captured image. For example, the control section 163 generates a control signal for controlling driving of the camera head 105. At this time, in a case where the imaging conditions have been input by the user, the control section 163 generates a control signal on the basis of the input provided by the user. Alternatively, in a case where the endoscope 101 includes the AE function, AF function, and the AWB function, the control section 163 appropriately calculates the optimal exposure value, focal length, and white balance in accordance with the result of the detection processing executed by the image processing section 161 and generates a control signal.

Additionally, the control section 163 cause the display apparatus 141 to displays the image of the affected site on the basis of the image signal subjected to the image processing by the image processing section 161. At this time, the control section 163 uses various recognizing techniques to recognize various objects in the affected site image. For example, by detecting, for example, the shape or color of an edge of an object included in the affected site image, the control section 163 can recognize a surgical instrument such as forceps, a particular biological region, bleeding, mist caused by the use of the energy treatment instrument 121, or the like. When causing the display apparatus 141 to display the image of the affected site, the control section 163 uses the result of the recognition to cause the display apparatus 141 to display various types of surgery assistance information on the image of the affected site in a superimposed manner. The surgery assistance information displayed in a superimposed manner is presented to the operator 167 to enable the surgery to proceed safely and reliably.

The transmission cable 165 connecting the camera head 105 and the CCU 139 together is an electric signal cable supporting communication of electric signals, an optical fiber supporting optical communication, or a composite cable corresponding to a combination of the electric signal cable and the optical fiber.

Here, in the illustrated example, wired communication is performed using the transmission cable 165. However, the communication between the camera head 105 and the CCU 139 may be wireless. Wireless communication between the camera head 105 and the CCU 139 eliminates a need to lay the transmission cable 165 in the operating room. This may prevent movement of medical staff in the operating room from being hindered by the transmission cable 165.

The example of the endoscopic surgery system 100 to which the technique according to the present disclosure may be applied has been described. Note that, here, the endoscopic surgery system 100 has been described by way of example but that the system to which the technique according to the present disclosure may be applied is not limited to such an example. For example, the technique according to the present disclosure may be applied to a soft endoscope system for examination or a microsurgery system.

2. Technical Features

Now, technical features of a medical observation system according to the embodiment of the present disclosure (in other words, a medical imaging system) will be described.

2.1. Basic Configuration

Figure 3:
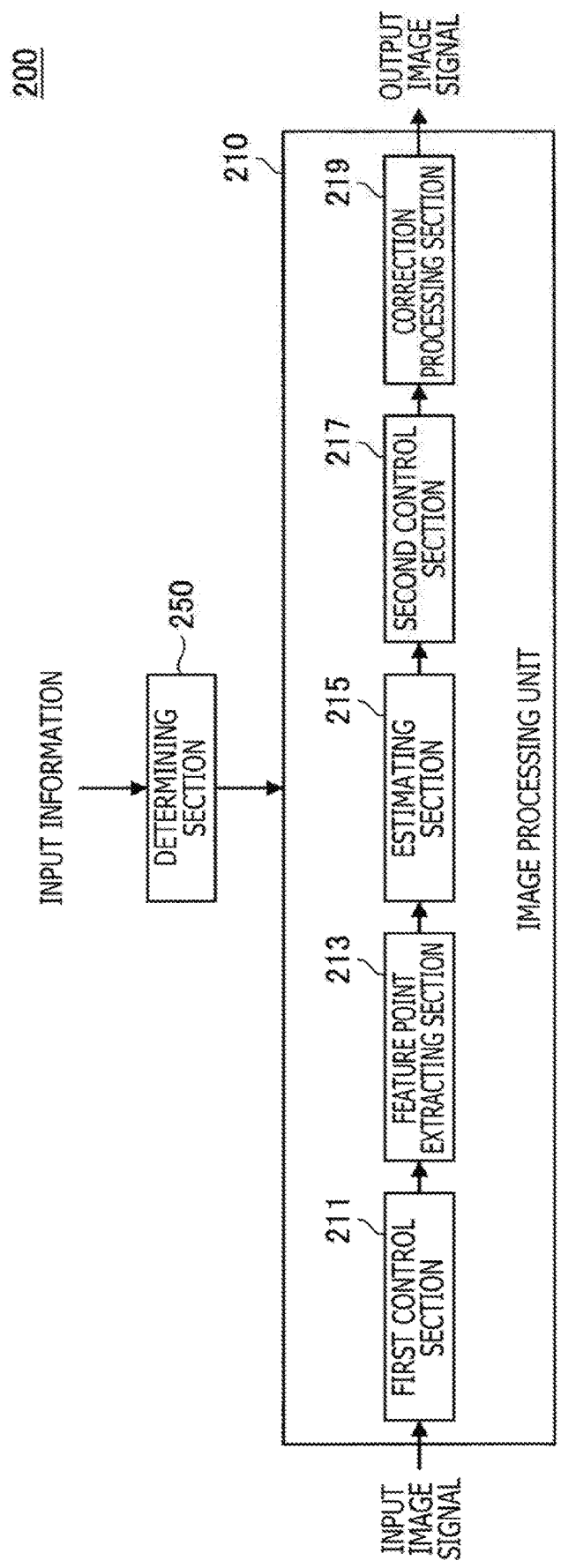
FIG. 3 is a block diagram illustrating an example of a functional configuration of a control apparatus in a medical observation system according to the embodiment of the present disclosure.

First, description will be given of an example of a basic functional configuration of a control apparatus (in other words, an image processing apparatus) executing image processing on an image captured by the imaging section, such as the CCU 139 described above with reference to FIG. 1. A particular focus is placed on sections of the control apparatus that correct image blurring caused by camera shake or the like. FIG. 3 is a block diagram illustrating an example of the functional configuration of the control apparatus in the medical observation system according to the present embodiment.

As illustrated in FIG. 3, a control apparatus 200 according to the present embodiment includes an image processing unit 210 and a determining section 250.

The image processing unit 210 executes various types of analysis processing on an image signal (hereinafter also referred to as the "input image signal") input from the imaging section at a predetermined frame rate to detect image blurring caused by camera shake or the like. On the basis of the result of the detection, the image processing unit 210 executes various types of processing on the input image signal to correct the image blurring.

Additionally, in the control apparatus 200 according to the present embodiment, the determining section 250 controls application or non-application of correction of image blurring and the degree of the correction (in other words, the intensity of the correction) in a case where the correction is to be applied, in accordance with predetermined input information such as detection results for various states or circumstances. By way of a specific example, the determining section 250 may control the application or non-application of the correction and the degree of the correction by determining a coefficient for controlling the degree of correction of image blurring in accordance with the predetermined input information and notifying the image processing unit 210 of the coefficient. Note that an example of control of the degree of correction of image blurring in accordance with input information will be separately described below in Examples in detail along with specific examples of the input information. Additionally, in the description below, the correction of image blurring may also be simply referred to as "blurring correction." In addition, the determining section 250 corresponds to an example of the "control section" controlling the application or non-application of correction of image blurring and the degree of the correction.

Here, the configuration of the image processing unit 210 will be described in further detail. As illustrated in FIG. 3, the image processing unit 210 includes, for example, a first control section 211, a feature point extracting section 213, an estimating section 215, a second control section 217, and a correction processing section 219.

The first control section 211 sets whether or not to apply the blurring correction to an input image signal on the basis of the control of the determining section 250. For example, according to the result of the determination made by the determining section 250 for whether or not to apply the blurring correction, the first control section 211 may associate the input image signal with a coefficient corresponding to the result of the determination (that is, the coefficient depending on whether or not to apply the blurring correction). By way of a more specific example, the first control section 211 may set "1" as the coefficient indicating whether or not to apply the blurring correction in a case where the blurring correction is applied and set "0" as the coefficient in a case where the blurring correction is not applied (that is, the blurring correction is suppressed). Then, the first control section 211 associates the input image signal with the information indicating whether or not to apply the blurring correction (for example, the coefficient indicating whether or not to apply the blurring correction) and outputs the resultant input image signal to the feature point extracting section 213.

Note that, in a case where selective switching between the application and non-application of the blurring correction is not necessary (that is, in a case where the blurring correction is always applied), the first control section 211 need not be provided or may be disabled.

The feature point extracting section 213 applies image analysis to the input image signal to extract characteristic portions from the image as feature points on the basis of, for example, distribution of edges (for example, wrinkles and patterns) and colors. The feature point extracting section 213 then notifies the estimating section 215 of the input image signal and information related to the feature points extracted from the input image signal.

The estimating section 215 estimates blurring of the entire image (more specifically, the direction and amount of blurring) on the basis of the input image signal and the information related to the feature points, the signal and information being output from the feature point extracting section 213.

By way of a specific example, the estimating section 215 separates a screen of the input image signal into blocks each with a predetermined size and compares each frame of the input image signal with a frame of the input image signal a predetermined number of frames before (for example, the preceding frame) on a block-by-block basis to calculate motion vectors in block units (hereinafter referred to as "local motion vectors") and reliability of the motion vectors.

The estimating section 215 also integrates those of the local motion vectors in the respective blocks in each frame which have high reliability to determine a motion vector for the entire image in the frame (hereinafter also referred to as the "global motion vector"). The estimating section 215 may also level global motion vectors for a number of frames before the frame of interest to remove instantaneous errors. The estimating section 215 may also perform levelling using a number of global motion vectors for a number of frames after the frame of interest.

The estimating section 215 also calculates a moving distance of the objective lens in the imaging section on the basis of a detection result for acceleration or angular acceleration detected by various sensors (not illustrated) provided in the imaging section and the global motion vector and the reliability of the global motion vector. The estimating section 215 then estimates blurring of the entire image (for example, the direction and amount of image blurring) on the basis of the calculated moving distance of the objective lens.

The estimating section 215 then associates the input image signal with information indicating the estimation result for the blurring of the entire image and outputs the resultant input image signal to the second control section 217.

The second control section 217 acquires the input image signal from the estimating section 215. The second control section 217 also controls the degree of blurring correction (in other words, the correction intensity) applied to the input image signal on the basis of the control of the determining section 250 in accordance with the information associated with the acquired input image signal and indicating whether or not to apply the blurring correction.

By way of a specific example, the second control section 217 determines the correction intensity of the blurring correction (in other words, the correction amount of the blurring correction) on the basis of the coefficient, associated with the input image signal, indicating whether or not to apply the blurring correction (for example, "1" or "0") and the coefficient notified by the determining section 250 (that is, the coefficient corresponding to the degree of the blurring correction). By way of a specific example, the second control section 217 may calculate a correction coefficient (gain) indicative of the correction intensity of the blurring correction by multiplying the coefficient associated with the input image signal by the coefficient notified by the determining section 250. Accordingly, for example, in a case where the blurring correction is not applied to the input image signal, the coefficient associated with the input image signal is "0," and thus, the result of calculation of the correction coefficient indicating the correction intensity is also "0." As a result, the blurring correction is not applied. Additionally, in a case where the blurring correction is applied to the input image signal, the coefficient associated with the input image signal is "1," and thus, the correction coefficient indicative of the correction intensity of the blurring correction is determined according to the coefficient notified by the determining section 250.

The second control section 217 then outputs, to the correction processing section 219, the input image signal and information indicative of the correction intensity of the blurring correction determined for the input image signal. Note that the information indicative of the correction intensity of the blurring correction corresponds to information indicating whether or not to apply the blurring correction and the degree of the application of the blurring correction, and, for example, to information indictive of the above-described correction coefficient for the blurring correction by way of example.

The correction processing section 219 acquires the input image signal from the second control section 217, and applies the blurring correction to the input image signal in accordance with various types of information associated with the input image signal.

Specifically, the correction processing section 219 outputs, to a component located succeeding the correction processing section 219 (for example, the display apparatus), as an output image signal, an image signal obtained by cutting out, from the entire region (effective pixel area) of the input image signal, a cutout area smaller in size than the effective pixel area. At this time, the correction processing section 219 shifts the position of the cutout area by a shift amount corresponding to the blurring of the entire image to correct the blurring. Note that the position of the cutout area (in other words, the shift amount corresponding to the blurring of the entire image) may be determined on the basis of information indicating the estimation result for the blurring of the entire image associated with the input image signal (that is, the information indicative of the direction and amount of the blurring).

Additionally, the correction processing section 219 may control the degree of the blurring correction applied to the input image signal on the basis of the information associated with the input image signal and indicating the correction intensity of the blurring correction. By way of a specific example, the correction processing section 219 may control, in accordance with the correction intensity, a threshold for determining whether or not to apply the blurring correction. In this case, the correction processing section 219 may apply the blurring correction in a case where the amount of blurring is smaller than the threshold, and provides control such that the threshold increases consistently with the correction intensity (that is, the threshold increases so as to include more significant blurring within the range of blurring to be corrected).

The correction processing section 219 may also control the correction amount of the blurring correction on the basis of the information indicative of the correction intensity of the blurring correction. By way of a specific example, the correction processing section 219 may limit the correction amount of the blurring correction (that is, the shift amount for the position of the cutout area) such that the correction amount decreases consistently with correction intensity.

The example of the basic functional configuration of the control apparatus executing image processing on the image captured by the imaging section has been described above with reference to FIG. 3, with a particular focus on the sections of the control apparatus that correct image blurring caused by camera shake or the like.

2.2. Processing

Figure 4:
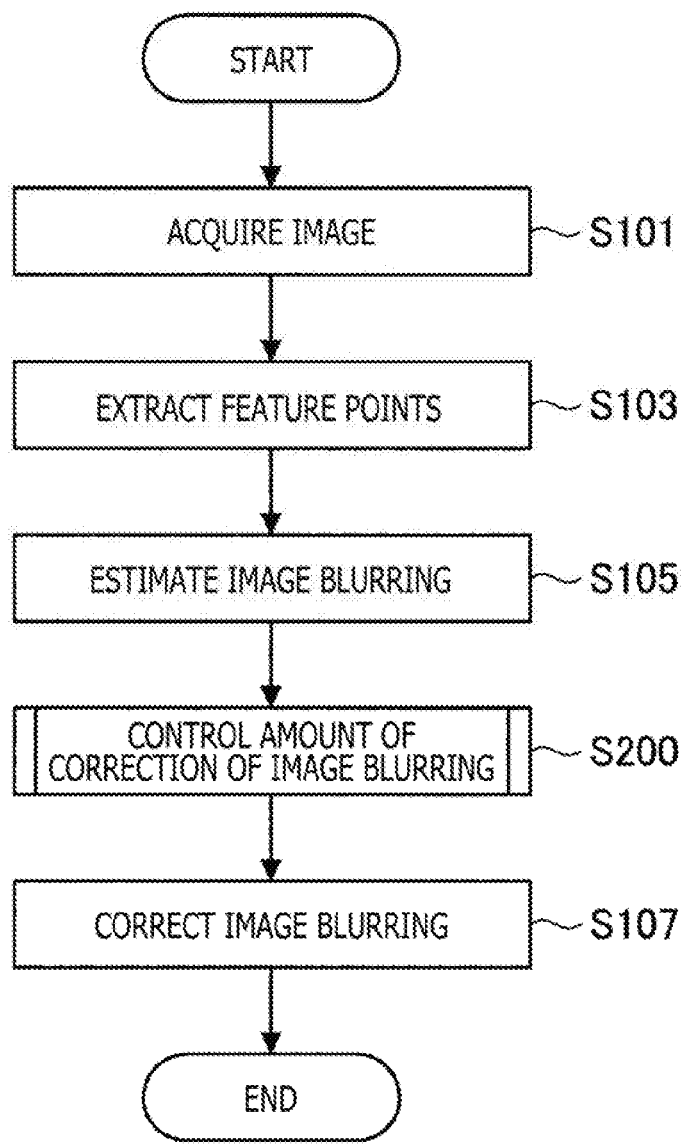
FIG. 4 is a flowchart illustrating an example of a flow of a sequence of processing executed by the control apparatus in the medical observation system according to the embodiment.

Now, an example of a flow of a sequence of processing by the control apparatus executing image processing on the image captured by the imaging section will be described with reference to FIG. 4, with a particular focus on the sections of the control apparatus that correct image blurring caused by camera shake or the like. FIG. 4 is a flowchart illustrating an example of a flow of a sequence of processing by the control apparatus in the medical observation system according to the present embodiment.

First, the control apparatus 200 acquires an image signal output from the imaging section at a predetermined frame rate (S101). At this time, the control apparatus 200 (first control section 211) may associate, with the acquired image signal (that is, the input image signal), information indicative of the application or non-application of the blurring correction determined in accordance with the predetermined input information.

The control apparatus 200 (feature point extracting section 213) then applies image analysis to the input image signal to extract characteristic portions from the image as feature points (S103).

The control apparatus 200 (estimating section 215) also estimates the blurring of the entire image on the basis of the result of extraction of feature points. By way of a specific example, the control apparatus 200 separates the screen of the input image signal into blocks each with a predetermined size and compares each frame of the input image signal with a frame of the input image signal a predetermined number of frames before on a block-by-block basis to calculate local motion vectors and reliability of the local motion vectors. The control apparatus 200 also integrates those of the local motion vectors in the respective blocks in each frame which have high reliability to determine the global motion vector. The control apparatus 200 also calculates the moving distance of the objective lens in the imaging section on the basis of the detection result for the acceleration or angular acceleration detected by the various sensors provided in the imaging section and the global motion vector and the reliability of the global motion vector. The control apparatus 200 then estimates the blurring of the entire image (for example, the direction and amount of image blurring) on the basis of the calculated moving distance of the objective lens (S105).

The control apparatus 200 (second control section 217) then controls the correction intensity of the blurring correction (that is, the degree of the blurring correction) applied to the input image signal in accordance with the predetermined input information. By way of a specific example, the control apparatus 200 may determine, in accordance with the input information, the coefficient indicative of the correction intensity of the blurring correction applied to the input image signal (S200).

The control apparatus 200 (correction processing section 219) then applies the blurring correction to the input image signal on the basis of the estimation result for the blurring of the entire image and the correction intensity corresponding to the predetermined input information, and outputs the corrected image signal to the component located succeeding the correction processing section 219 (for example, the display apparatus), as the output image signal. Note that the method for the blurring correction is as described above and will thus not be described below in detail (S107).

The example of the flow of the sequence of processing by the control apparatus executing image processing on the image captured by the imaging section has been described with reference to FIG. 4, with a particular focus on the sections of the control apparatus that correct image blurring caused by camera shake or the like.

2.3. Examples

Now, by way of examples of the medical observation system according to the present embodiment, an example of control related to the correction of image blurring performed by the control apparatus 200 as described above with reference to FIG. 3 will be described below, along with specific examples of the input information.

Example 1: Control According to Zoom Magnification

Figure 5:
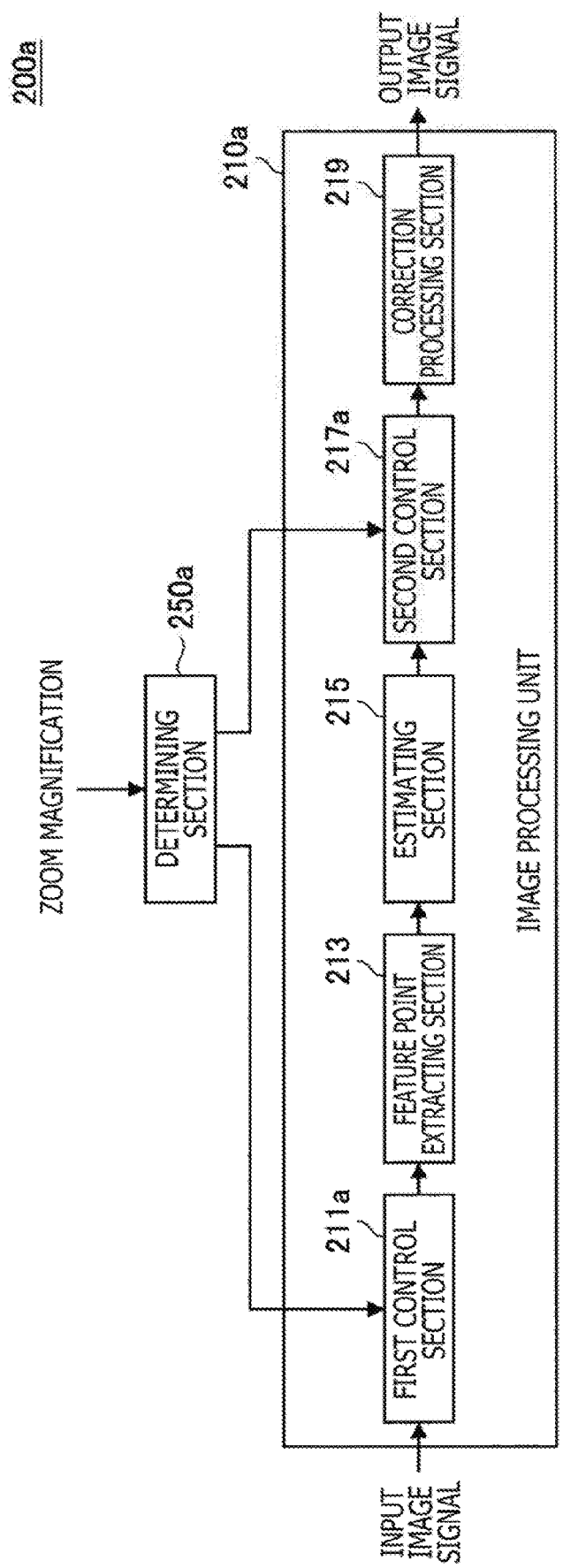
FIG. 5 is a descriptive diagram illustrating an example of control related to correction of image blurring performed by a control apparatus according to Example 1.
Figure 6:
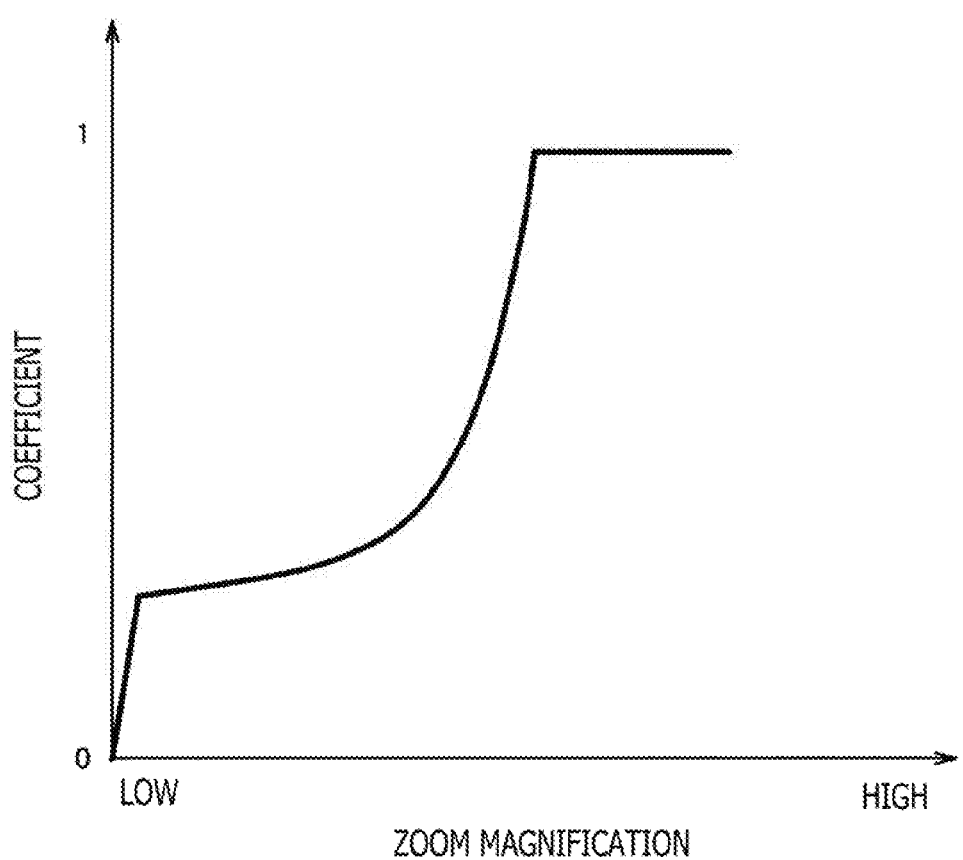
FIG. 6 is a descriptive diagram illustrating an example of the control related to the correction of image blurring performed by the control apparatus according to Example 1.

First, with reference to FIG. 5 and FIG. 6, Example 1 will be described that is an example of control using, as input information, information indicative of a zoom magnification of the imaging section and related to correction of image blurring according to the zoom magnification. FIG. 5 and FIG. 6 are descriptive diagrams illustrating an example of the control related to the correction of image blurring performed by a control apparatus according to Example 1. Note that in this description, the control apparatus according to the present example may be referred to as a "control apparatus 200a" so as to be distinguished from control apparatuses according to the other examples.

For example, FIG. 5 illustrates an example of a functional configuration of the control apparatus 200a according to Example 1. Note that the control apparatus 200a differs from the control apparatus 200 described with reference to FIG. 3 mainly in the operation of each of a determining section 250a, and a first control section 211a and a second control section 217a of an image processing unit 210a. Thus, for operations of the control apparatus 200a, FIG. 3 will be described with focus on sections different from the corresponding sections of the control apparatus 200. Sections of the control apparatus 200a that are substantially similar to the corresponding sections of the control apparatus 200 will not be described below in detail.

For example, the determining section 250a acquires information related to setting of the zoom magnification, from the imaging section as input information, and determines whether or not to apply blurring correction in accordance with the input information. In a case of applying the blurring correction, the determining section 250a determines a coefficient for controlling the degree of the application (that is, the correction intensity). That is, the first control section 211a controls whether or not to apply the blurring correction on the basis of the result of the determination made by the determining section 250a according to the zoom magnification. Additionally, the second control section 217a determines a correction coefficient indicative of the correction intensity of the blurring correction on the basis of the result of the determination made by the determining section 250a according to the zoom magnification.

Now, the example of the control related to the correction of image blurring according to the zoom magnification will be described in further detail with reference to FIG. 6. FIG. 6 is a graph illustrating an example of a relationship between the zoom magnification and the coefficient for controlling the correction intensity of the blurring correction in the present example. In FIG. 6, the abscissa axis indicates the zoom magnification, and the ordinate axis indicates the coefficient for controlling the correction intensity. Note that, in the present example, the coefficient for controlling the correction intensity is determined to range from not less than 0 to not more than 1, and the coefficient of 0 is substantially similar to the non-application of the blurring correction.

As illustrated in FIG. 6, in the present example, the coefficient for controlling the correction intensity is set to decrease and increase consistently with zoom magnification. Additionally, a zoom magnification smaller than or equal to a predetermined threshold may disable (suppress) the blurring correction.

By way of a specific example, a zoom magnification set to a lower value increases the range of an image captured (that is, the visual field range). When the correction intensity of the blurring correction is increased under these circumstances, for example, in a case where a motion vector indicative of motion of a surgical instrument such as intensely shaking forceps is employed as a global motion vector, a bird's-eye view image corresponding to a background may shake intensely to make an observation target such as a living organism difficult to observe. Thus, in such a case, the observation target such as the living organism may be made easier to observe by, for example, reducing the correction intensity of the blurring correction or disabling (suppressing) the blurring correction.

Additionally, by way of another example, in a case where the correction intensity of the blurring correction is increased with the zoom magnification set lower, when a cutout area is cut out from the effective pixel area, the regions removed as portions other than the cutout area (for example, end sides of the effective pixel area) tend to be larger. Thus, the blurring correction is applied even in a case where the range imaged by the imaging section is intentionally moved as in a case where a scope of the endoscope apparatus or the like is intentionally moved. As a result, the observation target such as the living organism may become difficult to observe. Even in such a case, the observation target such as the living organism may be made easier to observe by, for example, reducing the correction intensity of the blurring correction or disabling (suppressing) the blurring correction.

Note that the relationship between the zoom magnification and the coefficient for controlling the correction intensity of the blurring correction, illustrated in FIG. 6, is only an example. That is, the relationship between the zoom magnification and the coefficient is not necessarily limited to the example illustrated in FIG. 6 as long as control is provided such that the correction intensity of the blurring correction is increased consistently with zoom magnification.

With reference to FIG. 5 and FIG. 6, Example 1 has been described, which is an example of the control using, as input information, the information indicative of the zoom magnification of the imaging section and related to the correction of image blurring according to the zoom magnification.

Example 2: Control According to Working Distance to Subject

Figure 7:
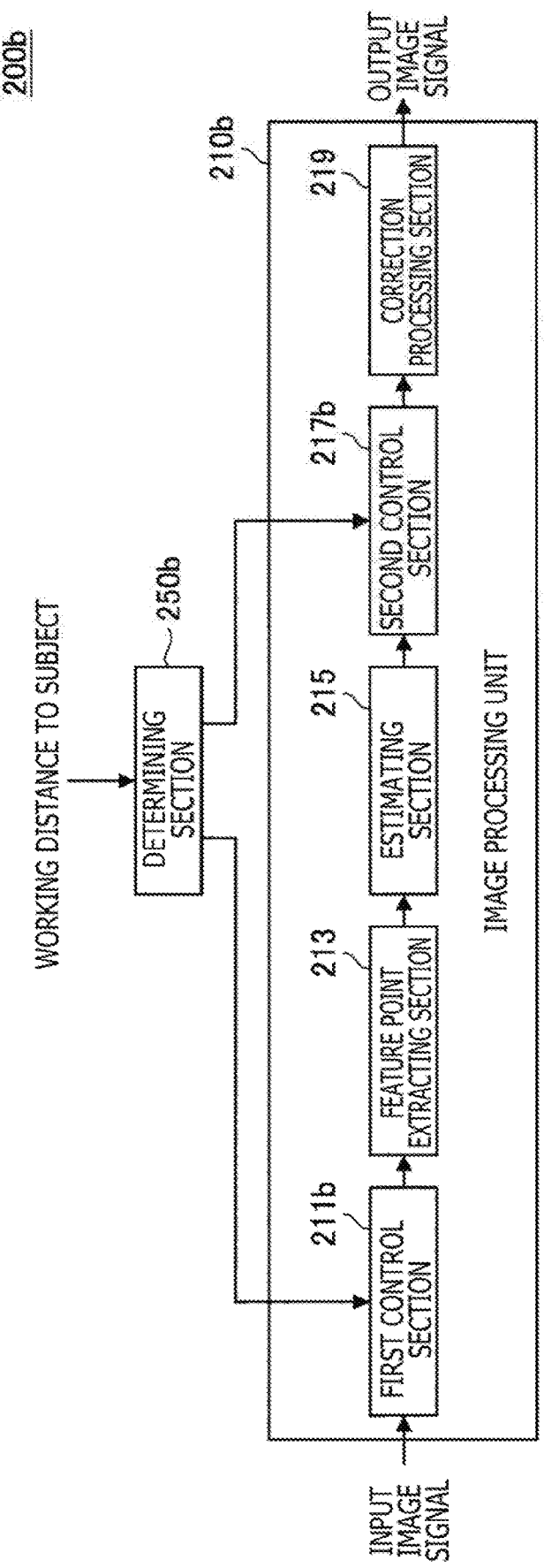
FIG. 7 is a descriptive diagram illustrating an example of control related to correction of image blurring performed by a control apparatus according to Example 2.
Figure 8:
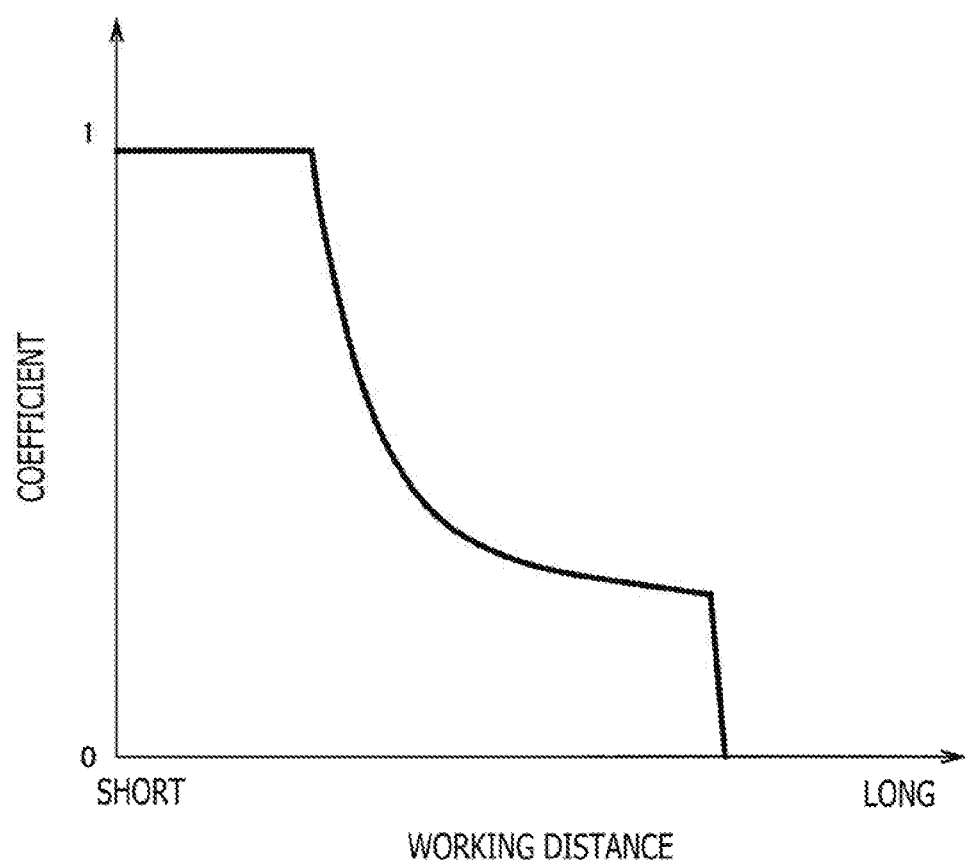
FIG. 8 is a descriptive diagram illustrating an example of the control related to the correction of image blurring performed by the control apparatus according to Example 2.

Now, with reference to FIG. 7 and FIG. 8, Example 2 will be described that is an example of control using, as input information, information indicative of a working distance to a subject and related to correction of image blurring according to the working distance. FIG. 7 and FIG. 8 are descriptive diagrams illustrating an example of control related to correction of image blurring performed by a control apparatus according to Example 2. Note that, in this description, the control apparatus according to the present example may be referred to as a "control apparatus 200$b$" so as to be distinguished from control apparatuses according to the other examples. Additionally, the working distance is intended to indicate a distance between the objective lens of the imaging section and a subject (for example, a living organism to be observed).

For example, FIG. 7 illustrates an example of a functional configuration of the control apparatus 200$b$ according to Example 2. Note that the control apparatus 200$b$ differs from the control apparatus 200 described with reference to FIG. 3 mainly in the operation of each of a determining section 250$b$, and a first control section 211$b$ and a second control section 217$b$ of an image processing unit 210$b$. Thus, for operations of the control apparatus 200$b$, FIG. 3 will be described with focus on sections different from the corresponding sections of the control apparatus 200. Sections of the control apparatus 200$b$ that are substantially similar to the corresponding sections of the control apparatus 200 will not be described below in detail.

For example, the determining section 250$b$ acquires, as input information, information indicative of a detection result for the distance between the objective lens of the imaging section and the subject (that is, the working distance), the detection result being provided by a distance measuring sensor or the like. Additionally, by way of another example, the determining section 250$b$ may acquire, as input information, information indicative of the distance between the objective lens of the imaging section and the subject in an image captured by the imaging section, the distance being calculated by analyzing the image. The determining section 250$b$ determines whether or not to apply the blurring correction in accordance with the acquired input information (that is, information indicative of the working distance), and in a case where the blurring correction is applied, determines a coefficient for controlling the degree of the application (that is, the correction intensity). That is, the first control section 211$b$ controls whether or not to apply the blurring correction on the basis of the result of determination made by the determining section 250$b$ according to the working distance. Additionally, the second control section 217$b$ determines a correction coefficient indicative of the correction intensity of the blurring correction on the basis of the result of the determination made by the determining section 250$b$ according to the working distance.

Here, with reference to FIG. 8, the example of the control related to the correction of image blurring according to the working distance will be described in further detail. FIG. 6 is a graph illustrating an example of a relationship between the working distance and the coefficient for controlling the correction intensity of the blurring correction. In FIG. 6, the abscissa axis indicates the zoom magnification, and the ordinate axis indicates the coefficient for controlling the correction intensity. Note that, in the present example, the coefficient for controlling the correction intensity is determined to range from not less than 0 to not more than 1, and the coefficient of 0 is substantially similar to the non-application of the blurring correction.

As illustrated in FIG. 8, in the present example, the coefficient for controlling the correction intensity is set to decrease and increase consistently with working distance (that is, to decrease and increase consistently with the distance between the objective lens of the imaging section and the subject). Additionally, a working distance larger than or equal to a threshold may disable (suppress) the blurring correction.

By way of a specific example, a decrease in working distance (that is, in distance between the objective lens of the imaging section and the subject) reduces the range of the image captured (that is, the visual field range), increasing the amount of blurring of the entire image relative to the moving distance of the objective lens of the imaging section. Thus, the observation target such as the living organism may be made easier to observe by, for example, increasing the correction intensity of the blurring correction (that is, increasing the coefficient for controlling the correction intensity) with decreasing working distance.

Note that the relationship between the working distance and the coefficient for controlling the correction intensity of the blurring correction, illustrated in FIG. 8, is only an example. That is, the relationship between the working distance and the coefficient is not necessarily limited to the example illustrated in FIG. 8 as long as control is provided such that the correction intensity of the blurring correction is increased consistently with decreasing working distance.

With reference to FIG. 7 and FIG. 8, Example 2 has been described, which is an example of the control using, as input information, the information indicative of the working distance to the subject and related to the correction of image blurring according to the working distance.

Example 3: Control According to Operative Duration

Figure 9:
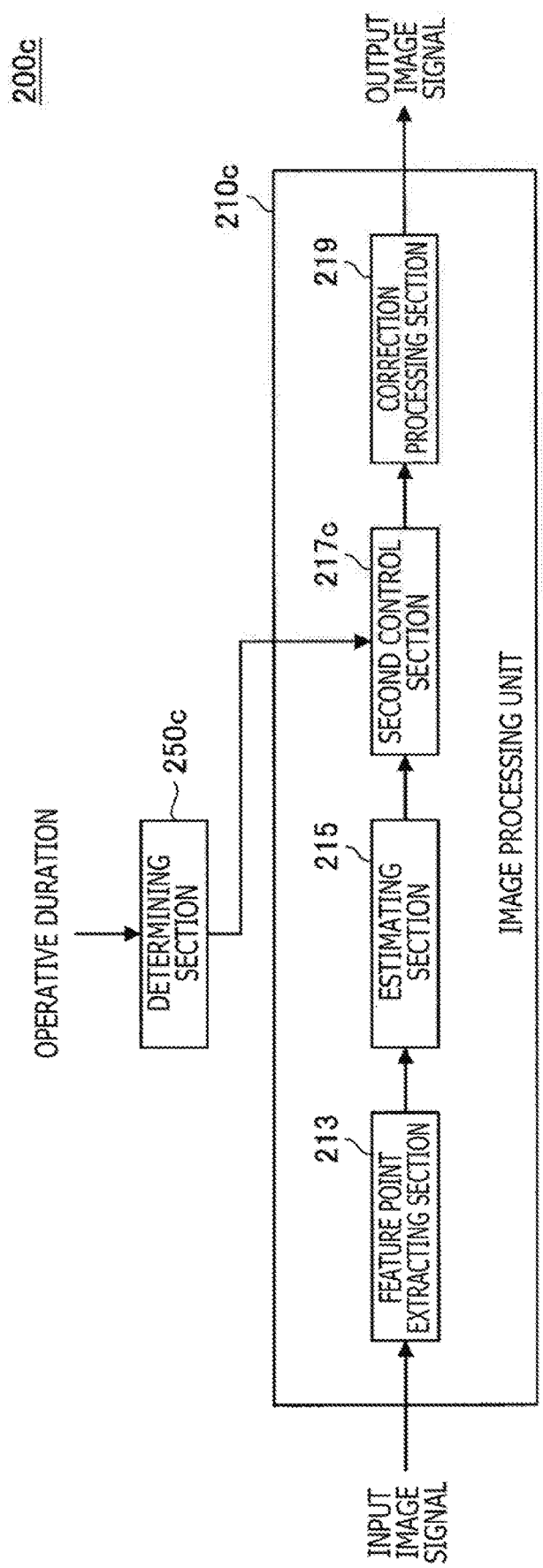
FIG. 9 is a descriptive diagram illustrating an example of control related to correction of image blurring performed by a control apparatus according to Example 3.
Figure 10:
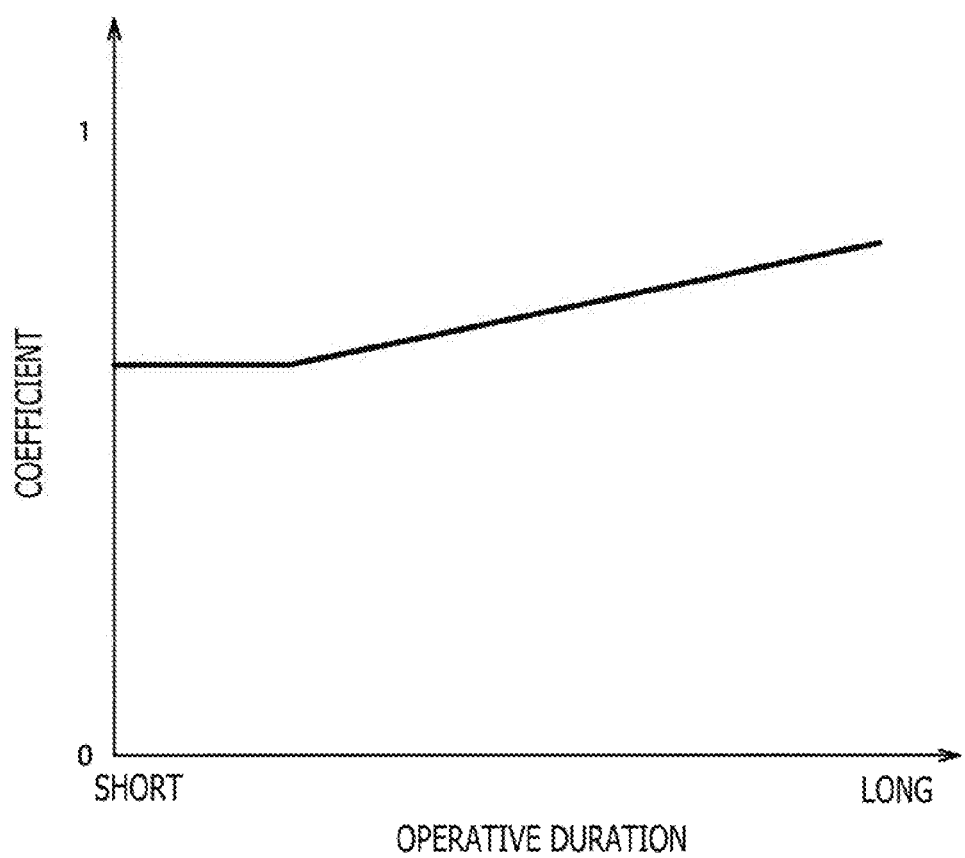
FIG. 10 is a descriptive diagram illustrating an example of the control related to the correction of image blurring performed by the control apparatus according to Example 3.

Now, with reference to FIG. 9 and FIG. 10, Example 3 will be described that is an example of control using, as input information, information indicative of an operative duration and related to correction of image blurring according to the operative duration. FIG. 9 and FIG. 10 are descriptive diagrams illustrating an example of control related to correction of image blurring performed by a control apparatus according to Example 3. Note that, in this description, the control apparatus according to the present example may be referred to as a "control apparatus 200*c*" so as to be distinguished from control apparatuses according to the other examples.

For example, FIG. 9 illustrates an example of a functional configuration of the control apparatus 200*c* according to Example 3. Note that a precondition for the present example is that image blurring is to be corrected. Thus, in the control apparatus 200*c*, an image processing unit 210*c* includes no component corresponding to the first control section 211 described above with reference to FIG. 3. Additionally, the control apparatus 200*c* differs from the control apparatus 200 described with reference to FIG. 3 mainly in the operation of each of a determining section 250*c*, and a second control section 217*b* of the image processing unit 210*c*. Thus, for operations of the control apparatus 200*c*, FIG. 3 will be described with focus on sections different from the corresponding sections of the control apparatus 200. Sections of the control apparatus 200*c* that are substantially similar to the corresponding sections of the control apparatus 200 will not be described below in detail.

For example, the determining section 250*c* acquires, as input information, information indicative of a measurement result for the operative duration obtained from a clocking section or the like, and determines a coefficient for controlling the degree of application of the blurring correction (that is, the correction intensity) in accordance with the acquired input information (that is, the information indicative of the operative duration). That is, the second control section 217*c* determines a correction coefficient indicative of the correction intensity of the blurring correction on the basis of the result of the determination made by the determining section 250*c* according to the operative duration.

Here, the example of the control related to the correction of image blurring according to the operative duration will be described in further detail with reference to FIG. 10. FIG. 10 is a graph illustrating an example of a relationship between the operative duration and the coefficient for controlling the correction intensity of the blurring correction in the present example. In FIG. 10, the abscissa axis indicates the operative duration, and the ordinate axis indicates the coefficient for controlling the correction intensity. Note that, in the present example, the coefficient for controlling the correction intensity is determined to range from not less than 0 to not more than 1, and the coefficient of 0 is substantially similar to the non-application of the blurring correction.

As illustrated in FIG. 10, in the present example, the coefficient for controlling the correction intensity is set to increase consistently with the operative duration in a case where the operative duration exceeds a predetermined threshold.

By way of a specific example, in a case where the endoscope is assumed to be held by a scopist, it is assumed that an extended operative duration increases the likelihood that the endoscope is shaken because the extended operative duration makes the scopist more and more tired. In light of these circumstances, control may be provided such that the correction intensity of the blurring correction is increased consistently with operative duration.

Note that the relationship between the operative duration and the coefficient for controlling the correction intensity of the blurring correction, illustrated in FIG. 10, is only an example. That is, the relationship between the operative duration and the coefficient is not necessarily limited to the example illustrated in FIG. 10 as long as control is provided such that the correction intensity of the blurring correction is increased consistently with operative duration.

With reference to FIG. 9 and FIG. 10, Example 3 has been described, which is an example of the control using, as input information, the information indicative of the operative duration and related to the correction of image blurring according to the operative duration.

Example 4: Control According to Vibration of Operating Table

Figure 11:
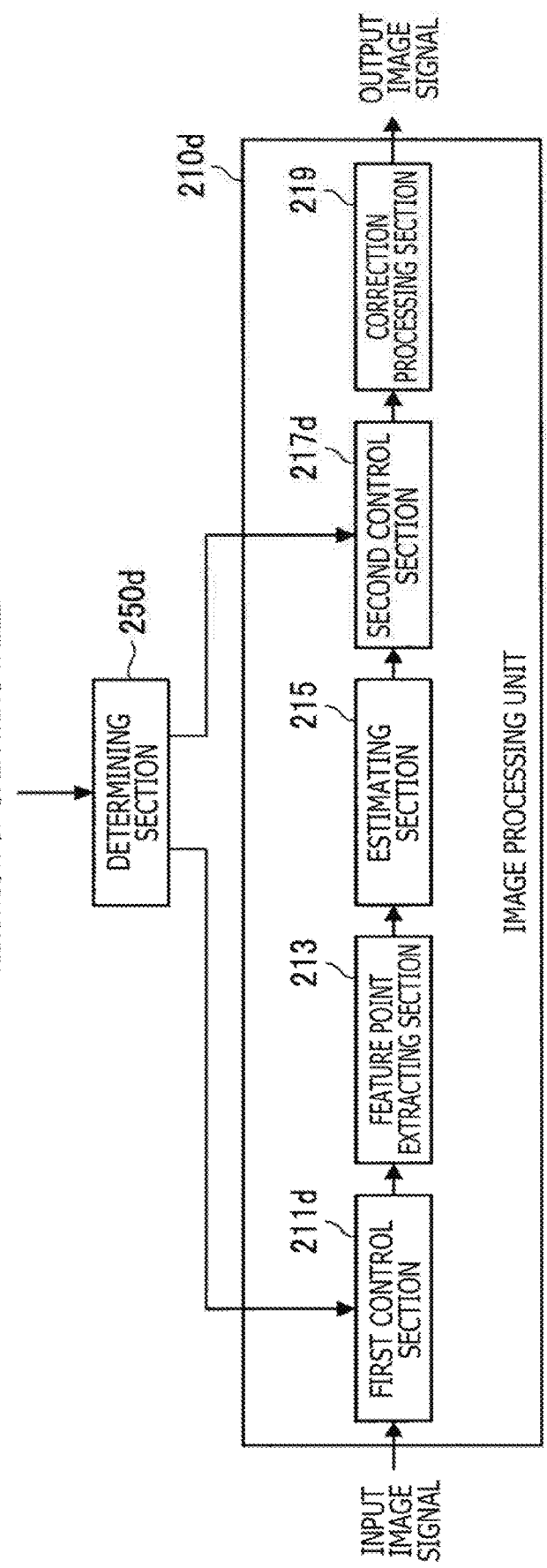
FIG. 11 is a descriptive diagram illustrating an example of control related to correction of image blurring performed by a control apparatus according to Example 4.
Figure 12:
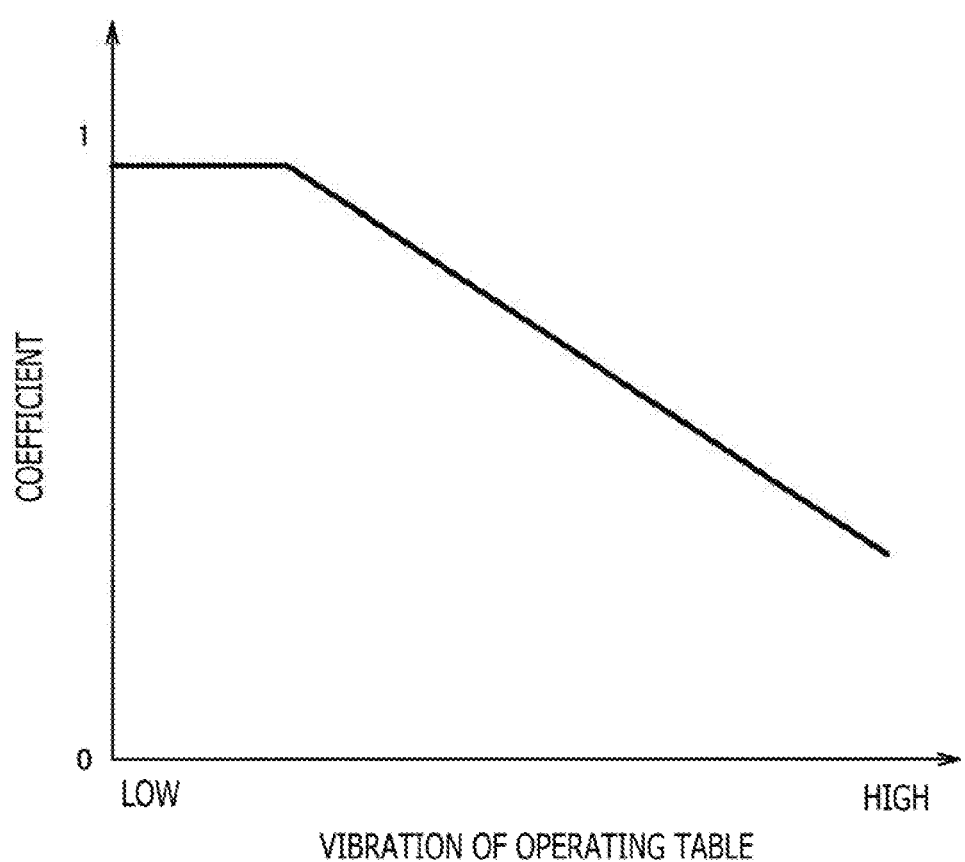
FIG. 12 is a descriptive diagram illustrating an example of the control related to the correction of image blurring performed by the control apparatus according to Example 4.

Now, with reference to FIG. 11 and FIG. 12, Example 4 will be described that is an example of control using, as input information, information indicating a detection result for vibration of an operating table and related to correction of image blurring according to the vibration of the operating table. FIG. 11 and FIG. 12 are descriptive diagrams illustrating an example of control related to correction of image blurring performed by a control apparatus according to Example 4. Note that, in this description, the control apparatus according to the present example may be referred to as a "control apparatus 200*d*" so as to be distinguished from control apparatuses according to the other examples.

For example, FIG. 11 illustrates an example of a functional configuration of the control apparatus 200*d* according to Example 4. Additionally, the control apparatus 200*d* differs from the control apparatus 200 described with reference to FIG. 3 mainly in the operation of each of a determining section 250*d*, and a first control section 211*d* and a second control section 217*d* of an image processing unit 210*d*. Thus, for operations of the control apparatus 200*d*, FIG. 3 will be described with focus on sections different from the corresponding sections of the control apparatus 200. Sections of the control apparatus 200*d* that are substantially similar to the corresponding sections of the control apparatus 200 will not be described below in detail.

For example, the determining section 250*d* acquires, as input information, information indicative of the detection result for the vibration of the operating table detected by various sensors such as a vibration sensor. The determining section 250*d* then determines whether or not to apply the blurring correction in accordance with the acquired input information (that is, information indicative of the vibration of the operating table), and in a case where the blurring correction is applied, determines a coefficient for controlling the degree of application of the blurring correction (that is, the correction intensity). That is, the first control section 211*d* controls whether or not to apply the blurring correction on the basis of the result of the determination made by the determining section 250*d* according to the vibration of the operating table. Additionally, the second control section 217*d* determines the correction coefficient indicative of the correction intensity of the blurring correction on the basis of the result of the determination made by the determining section 250d according to the vibration of the operating table.

Here, with reference to FIG. 12, detailed description will be given of an example of control related to correction of image blurring according to the vibration of the operating table. FIG. 6 is a graph illustrating the example of the relationship between the vibration of the operating table and the coefficient for controlling the correction intensity of the blurring correction in the present example. In FIG. 6, the abscissa axis indicates the magnitude of vibration of the operating table, and the ordinate axis indicates the coefficient for controlling the correction intensity. Note that, in the present example, the coefficient for controlling the correction intensity is determined to range from not less than 0 to not more than 1, and the coefficient of 0 is substantially similar to the non-application of the blurring correction.

As illustrated in FIG. 12, in the present example, the coefficient for controlling the correction intensity is set to decrease with increasing magnitude of vibration of the operating table in a case where the magnitude of the vibration exceeds a predetermined threshold. Additionally, in a case where the magnitude of vibration of the operating table is larger than or equal to the threshold, the blurring correction may be disabled (suppressed).

That is, in the present example, the correction intensity of the blurring correction is reduced with increasing magnitude of vibration of the operating table to inhibit exertion of adverse effect of the blurring correction.

Note that the relationship between the magnitude of vibration of the operating table and the coefficient for controlling the correction intensity of the blurring correction, illustrated in FIG. 12, is only an example. That is, the relationship between the magnitude of vibration of the operating table and the coefficient for controlling the correction intensity of the blurring correction is not necessarily limited to the example illustrated in FIG. 12 as long as control is provided such that the correction intensity of the blurring correction is reduced with increasing magnitude of vibration of the operating table.

With reference to FIG. 11 and FIG. 12, Example 4 has been described, which is an example of the control using, as input information, the information indicating the detection result for the vibration of the operating table and related to the correction of image blurring according to the operative duration.

Example 5: Control According to Occupancy of Surgical Instrument in Screen

Figure 13:
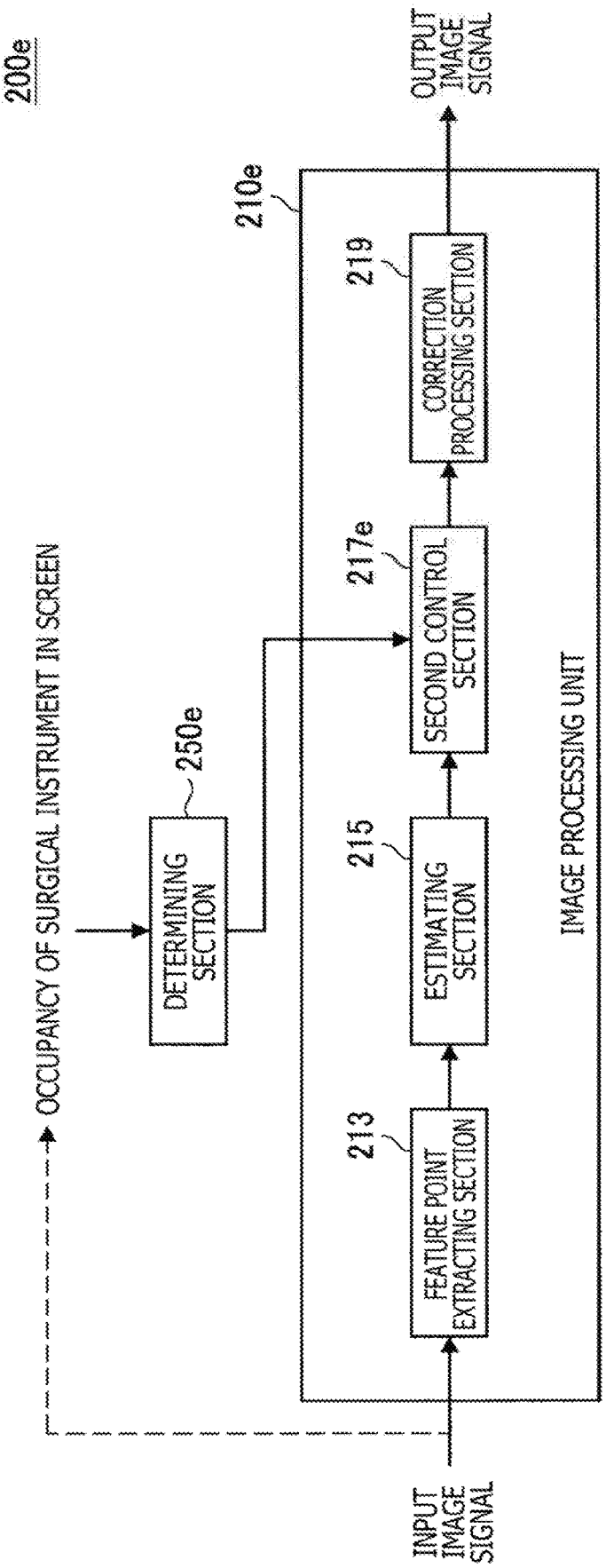
FIG. 13 is a descriptive diagram illustrating an example of control related to correction of image blurring performed by a control apparatus according to Example 5.
Figure 14:
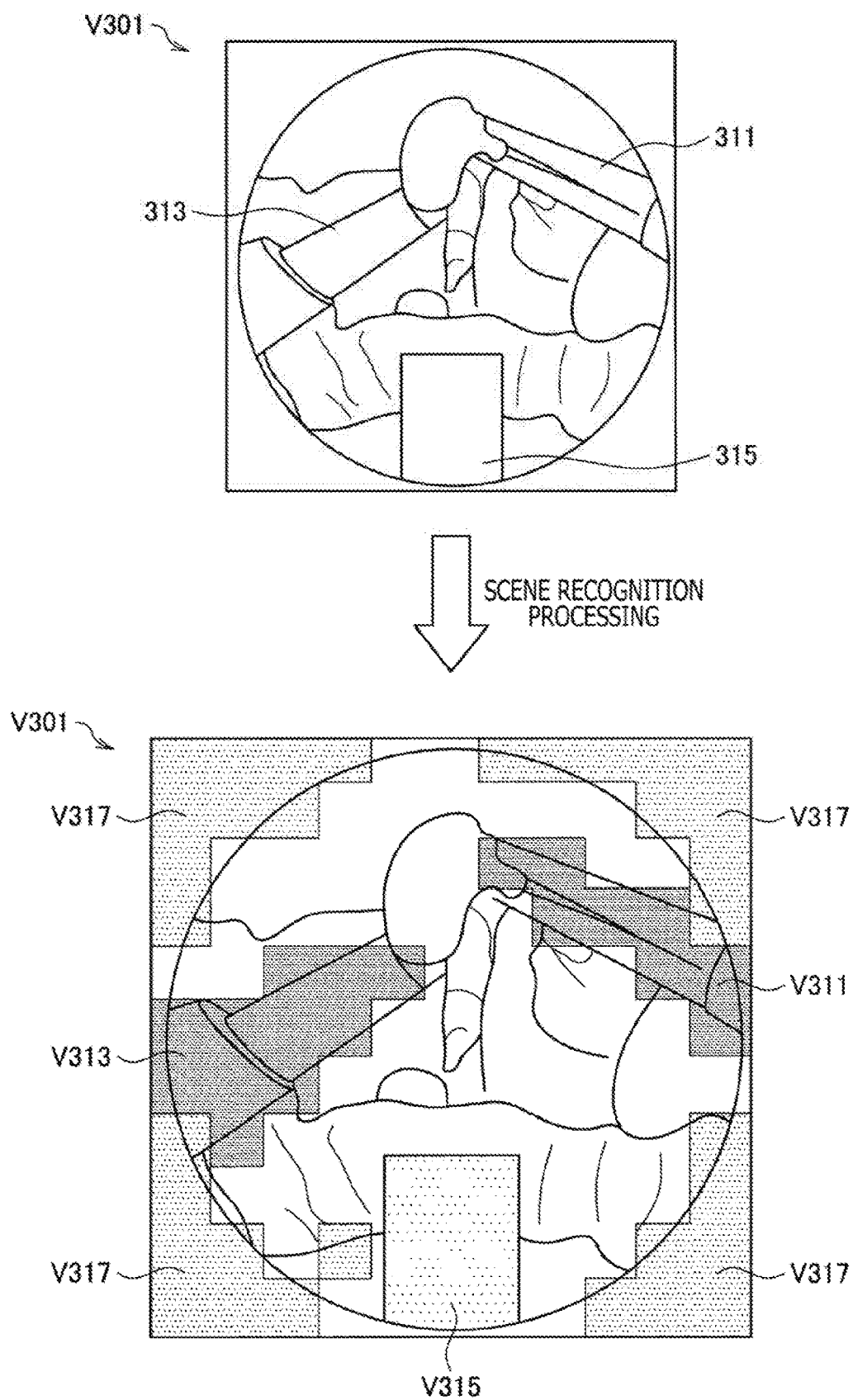
FIG. 14 is a descriptive diagram illustrating an example of the control related to the correction of image blurring performed by the control apparatus according to Example 5.
Figure 15:
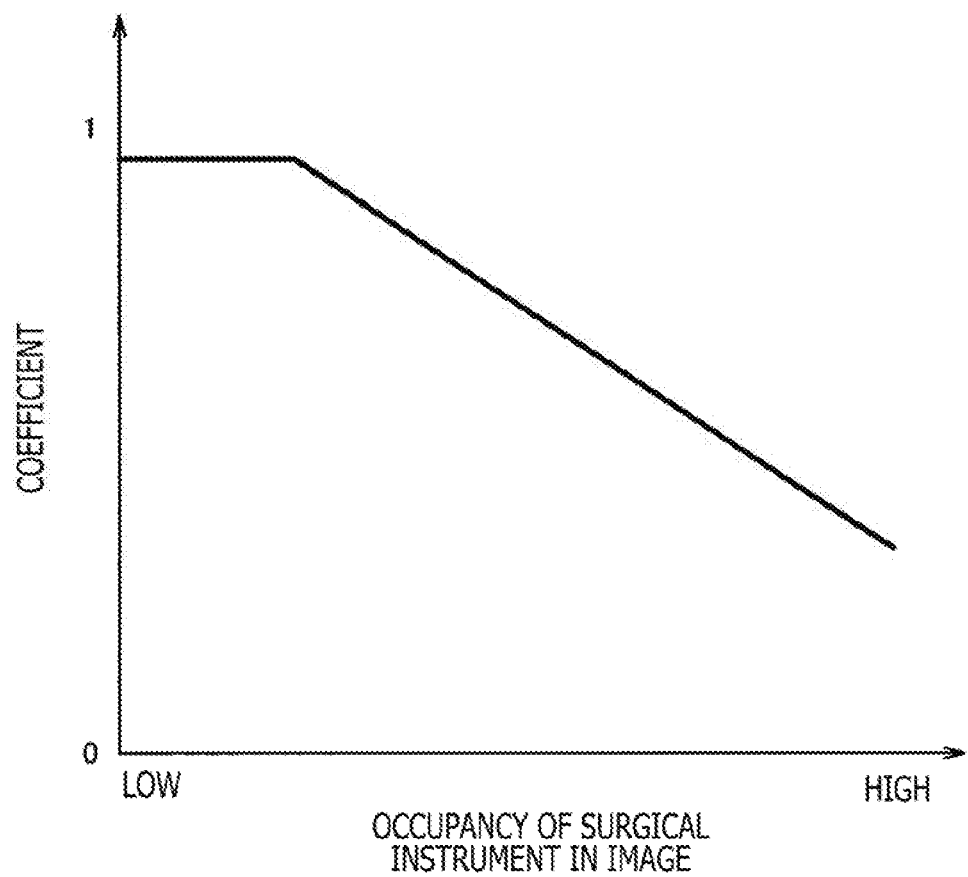
FIG. 15 is a descriptive diagram illustrating an example of the control related to the correction of image blurring performed by the control apparatus according to Example 5.

Now, with reference to FIGS. 13 to 15, Example 5 will be described that is an example of control using, as input information, information indicative of occupancy of a surgical instrument in a screen and related to correction of image blurring according to the occupancy of the surgical instrument. FIGS. 13 to 15 are descriptive diagrams illustrating an example of control related to correction of image blurring performed by a control apparatus according to Example 5. Note that, in this description, the control apparatus according to the present example may be referred to as a "control apparatus 200e" so as to be distinguished from control apparatuses according to the other examples.

For example, FIG. 13 illustrates an example of a functional configuration of the control apparatus 200e according to Example 5. Note that a precondition for the present example is that image blurring is to be corrected. Thus, in the control apparatus 200e, an image processing unit 210e includes no component corresponding to the first control section 211 described above with reference to FIG. 3. Additionally, the control apparatus 200e differs from the control apparatus 200 described with reference to FIG. 3 mainly in the operation of each of a determining section 250e, and a second control section 217e of the image processing unit 210e. Thus, for operations of the control apparatus 200e, FIG. 3 will be described with focus on sections different from the corresponding sections of the control apparatus 200. Sections of the control apparatus 200e that are substantially similar to the corresponding sections of the control apparatus 200 will not be described below in detail.

The determining section 250e acquires, as input information, information indicative of the occupancy of a surgical instrument in a screen recognized on the basis of an object recognizing technique or the like.

For example, FIG. 14 is a descriptive diagram illustrating an example of processing related to recognition of the occupancy of the surgical instrument in the screen. Specifically, in an upper diagram of FIG. 14, reference sign V301 denotes an example of an image of a living organism (image of a diseased site or the like) captured via the endoscope or the like. That is, in the image V301 surgical instruments such as forceps 311 and 313 and gauze 315 as well as a living organism to be observed in the screen are captured.

Additionally, a lower diagram of FIG. 14 illustrates an example of a recognition result for objects other than the living organism (for example, the surgical instruments) captured in the image V301, the recognition result being based on scene recognition processing executed, utilizing the object recognizing technique or the like, on the image V301 illustrated in the upper diagram. Specifically, regions denoted by reference signs V311 and V313 schematically represent an example of a recognition result for regions occupied by the forceps 311 and 313 in the screen. Additionally, a region denoted by reference sign V315 schematically represents an example of a recognition result for a region occupied by the gauze 315 in the screen. Additionally, reference sign V317 schematically represents an example of a recognition result for a region occupied by the lens barrel of the endoscope or the like in the screen V301.

That is, by utilizing the object recognizing technique or the like to recognize surgical instruments and the like captured in the image, for example, the occupancy of objects such as surgical instruments in the screen (in other words, the objects other than the living organism) can be calculated as illustrated in the lower diagram in FIG. 14.

Then, the determining section 250e determines a coefficient for controlling the degree of application of the blurring correction (that is, the correction intensity) in accordance with the acquired input information (that is, the information indicative of the occupancy of the surgical instruments in the screen). That is, as illustrated in FIG. 13, the second control section 217e determines a correction coefficient indicative of the correction intensity of the blurring correction on the basis of the result of the determination made by the determining section 250e according to the occupancy of the surgical instruments in the screen.

Here, with reference to FIG. 15, detailed description will be given of an example of control related to correction of image blurring according to the occupancy of the surgical instruments in the screen. FIG. 15 is a graph illustrating the example of the relationship between the occupancy of the surgical instruments in the screen and the coefficient for controlling the correction intensity of the blurring correction in the present example. In FIG. 10, the abscissa axis indicates the occupancy of the surgical instruments in the screen, and the ordinate axis indicates the coefficient for controlling the correction intensity. Note that, in the present example, the coefficient for controlling the correction intensity is determined to range from not less than 0 to not more than 1, and the coefficient of 0 is substantially similar to the non-application of the blurring correction.

As illustrated in FIG. 15, in the present example, the coefficient for controlling the correction intensity is set to decrease with increasing occupancy of the surgical instruments in the screen in a case where the occupancy exceeds a predetermined threshold.

By way of a specific example, an increased occupancy of the surgical instruments in the screen increases the ratio of a region where the living organism to be observed is shielded by the surgical instruments (that is, the subjects other than the living organism). Under such circumstances, in a case where feature points are extracted only from the living organism region, the number of feature points extracted decreases consistently with the ratio of the living organism region (that is, decreases with increasing ratio of the region shielded by the surgical instruments and the like). In such a case, reliability of motion vectors calculated on the basis of the result of extraction of feature points decreases to also reduce reliability of a correction value (for example, a shift amount) for the blurring correction based on the motion vectors. Note that, due to such properties, for example, the use of the result of object recognition is desirably avoided in setting the range of extraction of feature points. Additionally, even in a case where the extraction of feature points covers portions other than the living organism region, the coverage includes a large number of regions other than the living organism, thus reducing the reliability of motion vectors calculated on the basis of the result of extraction of feature points. This may result in a decrease in the reliability of the correction value for the blurring correction based on the motion vectors.

Accordingly, it is assumed that, in a case where the correction intensity of the blurring correction is increased with the reliability of the correction value for the blurring correction reduced, the blurring correction fails to be applied in an appropriate manner, making the observation target such as the living organism difficult to observe. Thus, the observation target such as the living organism can be prevented from becoming difficult to observe by, for example, reducing the correction intensity of the blurring correction with increasing occupancy of the regions other than the living organism (for example, the occupancy of the surgical instruments) in the screen.

Note that the relationship between the occupancy of the surgical instruments in the screen and the coefficient for controlling the correction intensity of the blurring correction, illustrated in FIG. 15, is only an example. That is, the relationship between the occupancy of the surgical instruments in the screen and the coefficient is not necessarily limited to the example illustrated in FIG. 15 as long as control is provided such that the correction intensity of the blurring correction is reduced with increasing occupancy. Additionally, the example of the case of reduction in the correction intensity of the blurring correction has been described above. However, control may be provided such that an increased occupancy of the surgical instruments disables (suppresses) the blurring correction.

With reference to FIGS. 13 to 15, Example 5 has been described, which is an example of the control using, as input information, the information indicative of the occupancy of the surgical instruments in the screen and related to the correction of image blurring according to the occupancy of the surgical instruments.

Example 6: Control According to Observation Mode

Figure 16:
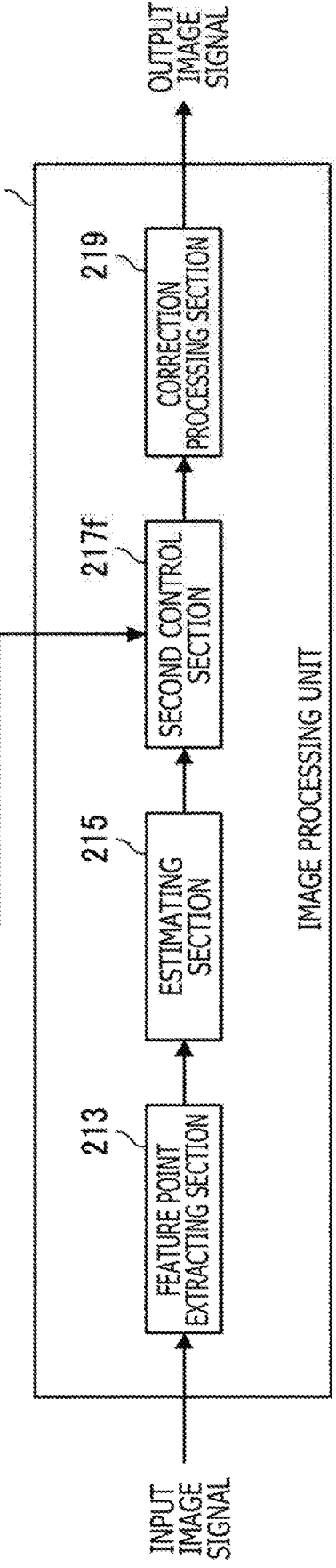
FIG. 16 is a descriptive diagram illustrating an example of control related to correction of image blurring performed by a control apparatus according to Example 6.

Now, with reference to FIG. 16, Example 6 will be described that is an example of control using, as input information, information indicative of an observation mode and related to correction of image blurring according to the observation mode. FIG. 16 is a descriptive diagram illustrating an example of control related to correction of image blurring performed by a control apparatus according to Example 6. Note that, in this description, the control apparatus according to the present example may be referred to as a "control apparatus $200f$" so as to be distinguished from control apparatuses according to the other examples. Additionally, the observation mode refers to, for example, a mode corresponding to observation method, for example, white light observation, special light observation such as infrared observation or fluorescent observation, or PDD (Photodynamic diagnosis).

For example, FIG. 16 illustrates an example of a functional configuration of the control apparatus $200f$ according to Example 6. Note that a precondition for the present example is that image blurring is to be corrected. Thus, in the control apparatus $200f$, an image processing unit $210f$ includes no component corresponding to the first control section 211 described above with reference to FIG. 3. Additionally, the control apparatus $200f$ differs from the control apparatus 200 described with reference to FIG. 3 mainly in the operation of each of a determining section $250f$, and a second control section $217f$ of the image processing unit $210f$. Thus, for operations of the control apparatus $200f$, FIG. 3 will be described with focus on sections different from the corresponding sections of the control apparatus 200. Sections of the control apparatus $200f$ that are substantially similar to the corresponding sections of the control apparatus 200 will not be described below in detail.

The determining section $250f$, for example, acquires, as input information, information related to setting of the observation mode, and determines a coefficient for controlling the degree of application of the blurring correction (that is, the correction intensity) in accordance with the acquired input information (that is, the information indicative of the observation mode). That is, the second control section $217f$ determines a correction coefficient indicative of the correction intensity of the blurring correction on the basis of the result of the determination made by the determining section $250f$ according to the observation mode.

Specifically, the special light observation tends to involve lower accuracy for calculation of motion vectors than the white light observation. Thus, under circumstances such as the special light observation where the frame rate is reduced, the correction intensity of the blurring correction may be set higher than in the white light observation so as to allow the observation target such as the living organism to be observed as is the case with the white light observation.

With reference to FIG. 16, Example 6 has been described, which is an example of the control using, as input information, the information indicative of the observation mode and related to the correction of image blurring according to the observation mode.

Example 7: Control According to Distance Between Monitor and Operator

Figure 17:
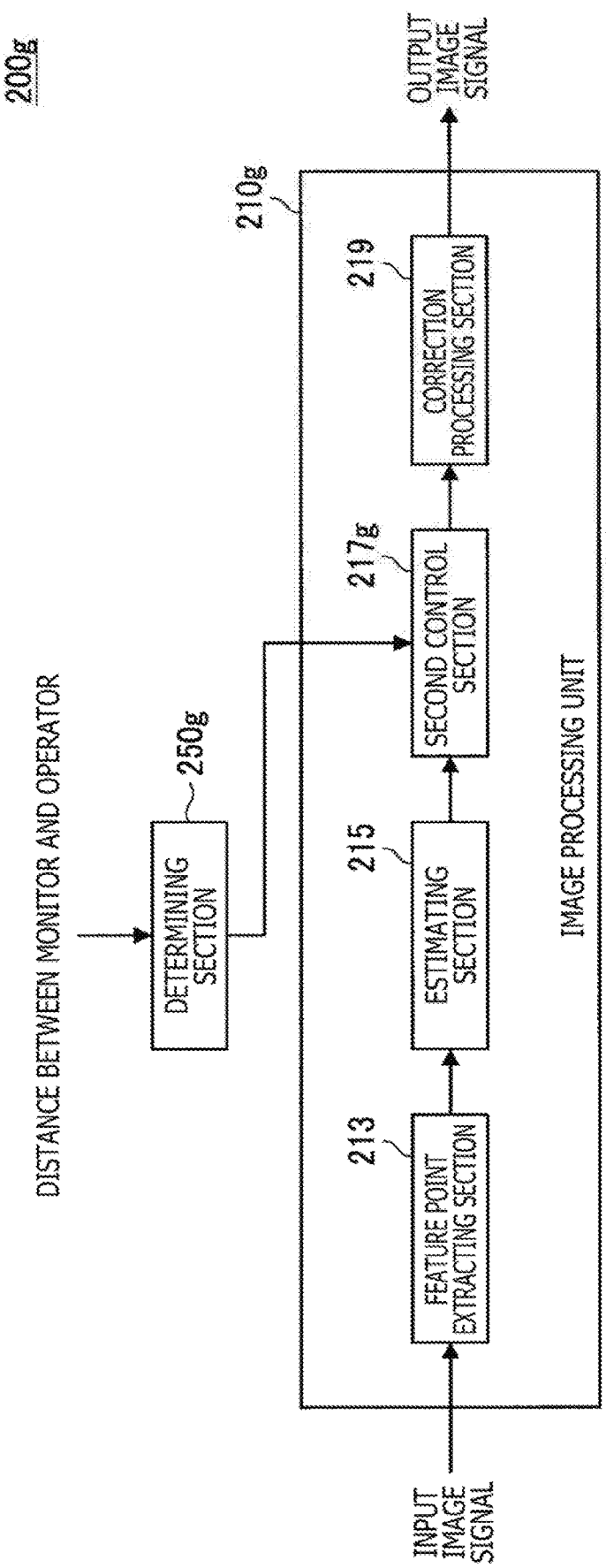
FIG. 17 is a descriptive diagram illustrating an example of control related to correction of image blurring performed by a control apparatus according to Example 7.
Figure 18:
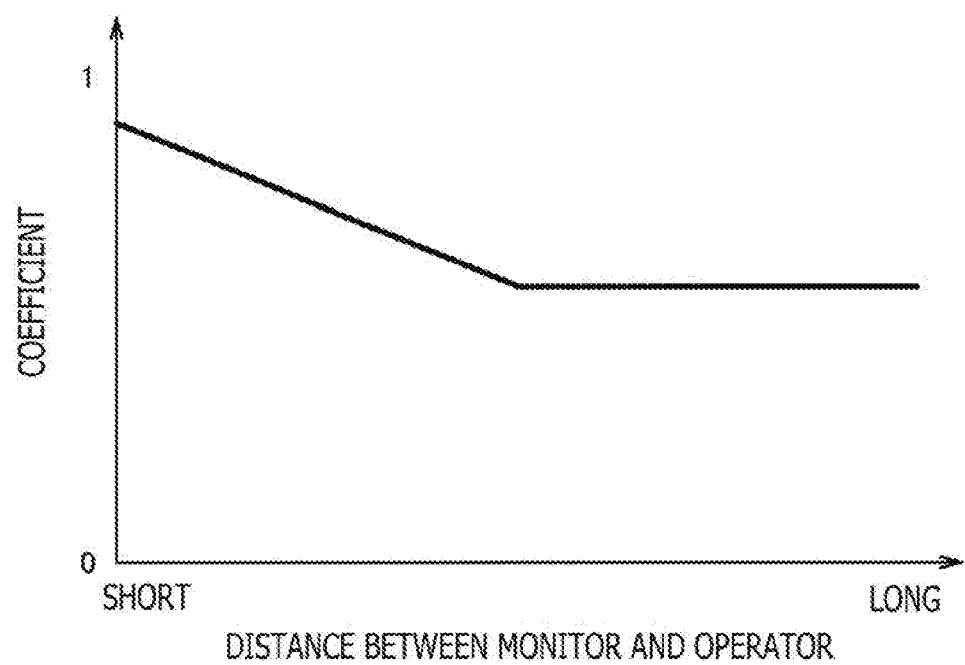
FIG. 18 is a descriptive diagram illustrating an example of control related to correction of image blurring performed by a control apparatus according to Example 7.

Now, with reference to FIG. 17 and FIG. 18, Example 7 will be described that is an example of control using, as input information, information indicative of a distance between a monitor and the operator and related to correction of image blurring according to the distance. FIG. 17 and FIG. 18 are descriptive diagrams illustrating an example of control related to correction of image blurring performed by a control apparatus according to Example 7. Note that, in this description, the control apparatus according to the present example may be referred to as a "control apparatus 200g" so as to be distinguished from control apparatuses according to the other examples.

For example, FIG. 17 illustrates an example of a functional configuration of the control apparatus 200g according to Example 7. Note that a precondition for the present example is that image blurring is to be corrected. Thus, in the control apparatus 200g, an image processing unit 210g includes no component corresponding to the first control section 211 described above with reference to FIG. 3. Additionally, the control apparatus 200g differs from the control apparatus 200 described with reference to FIG. 3 mainly in the operation of each of a determining section 250g, and a second control section 217g of the image processing unit 210g. Thus, for operations of the control apparatus 200g, FIG. 3 will be described with focus on sections different from the corresponding sections of the control apparatus 200. Sections of the control apparatus 200g that are substantially similar to the corresponding sections of the control apparatus 200 will not be described below in detail.

The determining section 250g acquires, as input information, information related to a measurement result for a distance between the operator and a predetermined monitor (for example, a main monitor), and determines a coefficient for controlling the degree of application of the blurring correction (that is, the correction intensity) in accordance with the acquired input information (that is, the information indicative of the distance between the operator and the monitor). That is, the second control section 217g determines a correction coefficient indicative of the correction intensity of the blurring correction on the basis of the result of the determination made by the determining section 250g according to the distance between the operator and the monitor. Note that a method for acquiring the information indicative of the distance between the operator and the monitor is not particularly limited as long as the method allows the information to be acquired. By way of a specific example, the distance between the operator and the monitor may be measured (calculated) on the basis of an image captured with a camera for a surgical field or the like and illustrating the operator and monitor. Additionally, by way of another example, the information indicative of the distance between the operator and the monitor may be acquired on the basis of the detection result from the distance measuring sensor and the like.

Here, with reference to FIG. 18, detailed description will be given of an example of control related to correction of image blurring according to the distance between the operator and the monitor. FIG. 18 is a graph illustrating the example of the relationship between the distance between the operator and the monitor and the coefficient for controlling the correction intensity of the blurring correction in the present example. In FIG. 18, the abscissa axis indicates the distance between the operator and the monitor, and the ordinate axis indicates the coefficient for controlling the correction intensity. Note that, in the present example, the coefficient for controlling the correction intensity is determined to range from not less than 0 to not more than 1, and the coefficient of 0 is substantially similar to the non-application of the blurring correction.

As illustrated in FIG. 18, in the present example, the coefficient for controlling the correction intensity is set to increase with decreasing distance between the operator and the monitor (that is, increasing closeness from the operator to the monitor). Additionally, in a case where the distance between the operator and the monitor exceeds a predetermined threshold, the coefficient for controlling the correction intensity may be maintained at a predetermined value.

By way of a specific example, the degree of perception of image blurring obtained by the operator relatively increases with decreasing distance between the operator and the monitor. In light of such circumstances, control may be provided such that the correction intensity of the blurring correction is increased with decreasing distance between the operator and the monitor.

Note that the relationship between the distance between the operator and the monitor and the coefficient for controlling the correction intensity of the blurring correction, illustrated in FIG. 18, is only an example. That is, the relationship between the distance between the operator and the monitor and the coefficient is not necessarily limited to the example illustrated in FIG. 18 as long as control is provided such that the correction intensity of the blurring correction is increased with decreasing distance between the operator and the monitor.

With reference to FIG. 17 and FIG. 18, Example 7 has been described, which is an example of the control using, as input information, the information indicative of the distance between the operator and the monitor and related to the correction of image blurring according to the distance.

Example 8: Control According to Monitor Size

Figure 19:
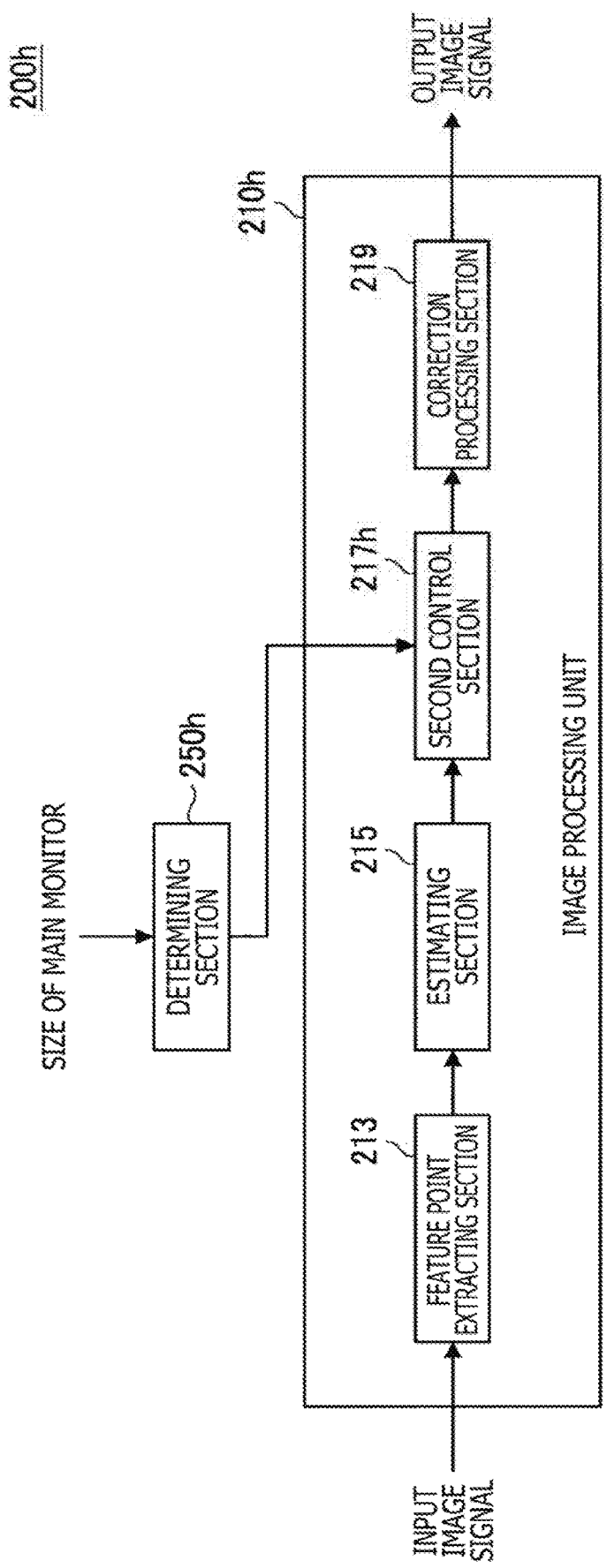
FIG. 19 is a descriptive diagram illustrating an example of control related to correction of image blurring performed by a control apparatus according to Example 8.
Figure 20:
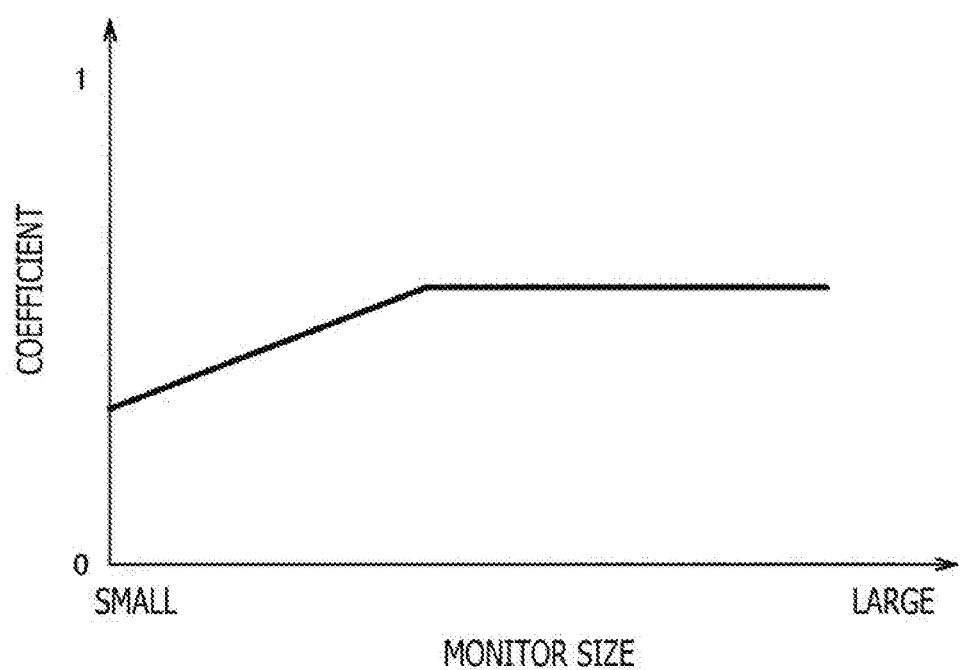
FIG. 20 is a descriptive diagram illustrating an example of the control related to the correction of image blurring performed by the control apparatus according to Example 8.

Now, with reference to FIG. 19 and FIG. 20, Example 8 will be described that is an example of control using, as input information, information indicative of a monitor size of a predetermined monitor and related to correction of image blurring according to the monitor size. FIG. 19 and FIG. 20 are descriptive diagrams illustrating an example of control related to correction of image blurring performed by a control apparatus according to Example 8. Note that, in this description, the control apparatus according to the present example may be referred to as a "control apparatus 200h" so as to be distinguished from control apparatuses according to the other examples.

For example, FIG. 19 illustrates an example of a functional configuration of the control apparatus 200h according to Example 8. Note that a precondition for the present example is that image blurring is to be corrected. Thus, in the control apparatus 200h, an image processing unit 210h includes no component corresponding to the first control section 211 described above with reference to FIG. 3. Additionally, the control apparatus 200h differs from the control apparatus 200 described with reference to FIG. 3 mainly in the operation of each of a determining section 250h, and a second control section 217h of the image processing unit 210h. Thus, for operations of the control apparatus 200h, FIG. 3 will be described with focus on sections different from the corresponding sections of the control apparatus 200. Sections of the control apparatus 200h that are substantially similar to the corresponding sections of the control apparatus 200 will not be described below in detail.

The determining section 250h acquires, as input information, information indicative of the monitor size of the predetermined monitor (for example, the main monitor), and determines a coefficient for controlling the degree of application of the blurring correction (that is, the correction intensity) in accordance with the acquired input information (that is, the information indicative of the monitor size). That is, the second control section 217h determines a correction coefficient indicative of the correction intensity of the blurring correction on the basis of the result of the determination made by the determining section 250h according to the monitor size. Note that a method for acquiring the information indicative of the monitor size of the predetermined monitor is not particularly limited as long as the method allows the information to be acquired. By way of a specific example, the information indicative of the monitor size of the predetermined monitor may be acquired from the monitor itself on which the image is displayed.

Here, with reference to FIG. 20, detailed description will be given of an example of control related to correction of image blurring according to the monitor size. FIG. 20 is a graph illustrating the example of the relationship between the monitor size and the coefficient for controlling the correction intensity of the blurring correction in the present example. In FIG. 20, the abscissa axis indicates the monitor size, and the ordinate axis indicates the coefficient for controlling the correction intensity. Note that, in the present example, the coefficient for controlling the correction intensity is determined to range from not less than 0 to not more than 1, and the coefficient of 0 is substantially similar to the non-application of the blurring correction.

As illustrated in FIG. 20, in the present example, the coefficient for controlling the correction intensity is set to increase consistently with monitor size. Additionally, in a case where the monitor size exceeds a predetermined threshold, the coefficient for controlling the correction intensity may be maintained at a predetermined value.

By way of a specific example, an increased monitor size increases the size of the image displayed on the monitor, relatively increasing a blur width in the image. In light of such circumstances, control may be provided such that the correction intensity of the blurring correction is increased consistently with monitor size.

Note that the relationship between the monitor size and the coefficient for controlling the correction intensity of the blurring correction, illustrated in FIG. 20, is only an example. That is, the relationship between the monitor size and the coefficient is not necessarily limited to the example illustrated in FIG. 20 as long as control is provided such that the correction intensity of the blurring correction is increased consistently with monitor size.

With reference to FIG. 19 and FIG. 20, Example 8 has been described, which is an example of the control using, as input information, the information indicative of the monitor size of the predetermined monitor and related to the correction of image blurring according to the monitor size.

Example 9: Control According to State of Surgical Instrument

Figure 21:
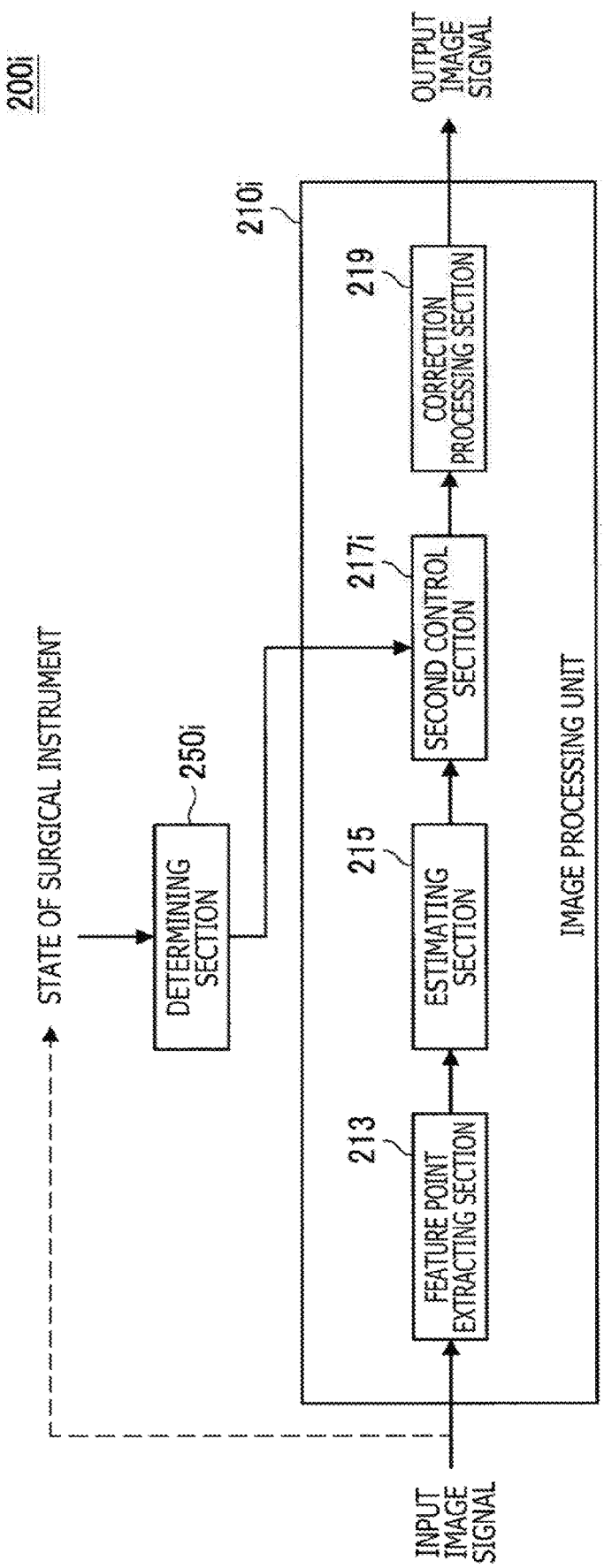
FIG. 21 is a descriptive diagram illustrating an example of control related to correction of image blurring performed by a control apparatus according to Example 9.

Now, with reference to FIGS. 21 to 23, Example 9 will be described that is an example of control using, as input information, information indicative of a state of a surgical instrument and related to correction of image blurring according to the state of the surgical instrument. FIGS. 21 to 23 are descriptive diagrams illustrating an example of control related to correction of image blurring performed by a control apparatus according to Example 9. Note that, in this description, the control apparatus according to the present example may be referred to as a "control apparatus 200i" so as to be distinguished from control apparatuses according to the other examples.

For example, FIG. 21 illustrates an example of a functional configuration of the control apparatus 200i according to Example 9. Note that a precondition for the present example is that image blurring is to be corrected. Thus, in the control apparatus 200i, an image processing unit 210i includes no component corresponding to the first control section 211 described above with reference to FIG. 3. Additionally, the control apparatus 200i differs from the control apparatus 200 described with reference to FIG. 3 mainly in the operation of each of a determining section 250i, and a second control section 217i of the image processing unit 210i. Thus, for operations of the control apparatus 200i, FIG. 3 will be described with focus on sections different from the corresponding sections of the control apparatus 200. Sections of the control apparatus 200i that are substantially similar to the corresponding sections of the control apparatus 200 will not be described below in detail.

The determining section 250i acquires, as input information, information indicative of the state of a surgical instrument, for example, a stapler, an energy device, a suture needle and thread, or a debrider, and determines a coefficient for controlling the degree of application of the blurring correction (that is, the correction intensity) in accordance with the acquired input information (that is, the information indicative of the state of the surgical instrument). That is, the second control section 217i determines a correction coefficient indicative of the correction intensity of the blurring correction on the basis of the result of the determination made by the determining section 250i according to the state of the surgical instrument. Note that a method for acquiring the information indicative of the state of the surgical instrument is not particularly limited as long as the method allows the information to be acquired. By way of a specific example, the information indicative of the state of the surgical instrument may be acquired from the target surgical instrument or the control section controlling the surgical instrument. Additionally, by way of another example, the state of the surgical instrument captured in the image may be recognized by applying image analysis to the image.

Here, with reference to FIG. 22, the example of the control related to the correction of image blurring according to the state of the surgical instrument will be described in further detail. FIG. 22 is a flowchart illustrating an example of a flow of control of the blurring correction according to the state of the surgical instrument in the present example.

As illustrated in FIG. 22, the control apparatus 200i (determining section 250i) determines whether or not a predetermined surgical instrument has been detected (S201), and in a case where the surgical instrument has been detected (S201, YES), determines whether or not a predetermined operation with the surgical instrument has been detected (S203). Then, in a case where the operation with the surgical instrument has been detected (S203, YES), the control apparatus 200i (second control section 217i) provides control to increase the correction intensity of the blurring correction (S205).

For example, FIG. 23 illustrates examples of the surgical instrument to be detected and examples of the operation with the surgical instrument. Specifically, examples of the surgical instrument to be detected include an "stapler," an "energy device," a "suture needle and thread," and a "debrider." Additionally, examples of the operation with the stapler include an operation of "nipping" the living organism or the like, and an operation of "discharging" a drug or the like. Additionally, examples of the operation with the energy device include an operation of "incising" the living organism or the like and a "hemostasis" operation. Additionally, an example of the operation with the suture needle and thread is a "suture" operation. Additionally, an example of the operation with the debrider is an operation of "excising" lesion or the like. In a case where these operations are performed, the image desirably remains stable without being blurred. Accordingly, when the operation is detected, possible image blurring may be suppressed by providing control to increase the correction intensity of the blurring correction.

On the other hand, as illustrated in FIG. 22, in a case where the predetermined surgical instrument fails to have been detected (S201, NO) or the predetermined operation with the predetermined surgical instrument fails to have been detected (S203, NO), the control apparatus 200$i$ (second control section 217$i$) may provide control to reduce the correction intensity of the blurring correction (S205). Additionally, at this time, the control apparatus 200$i$ (second control section 217$i$) may disable (suppress) the blurring correction.

With reference to FIGS. 21 to 23, Example 9 has been described, which is an example of the control using, as input information, the information indicative of the state of the surgical instrument and related to the correction of image blurring according to the state of the surgical instrument.

Example 10: Control According to User Input

Figure 24:
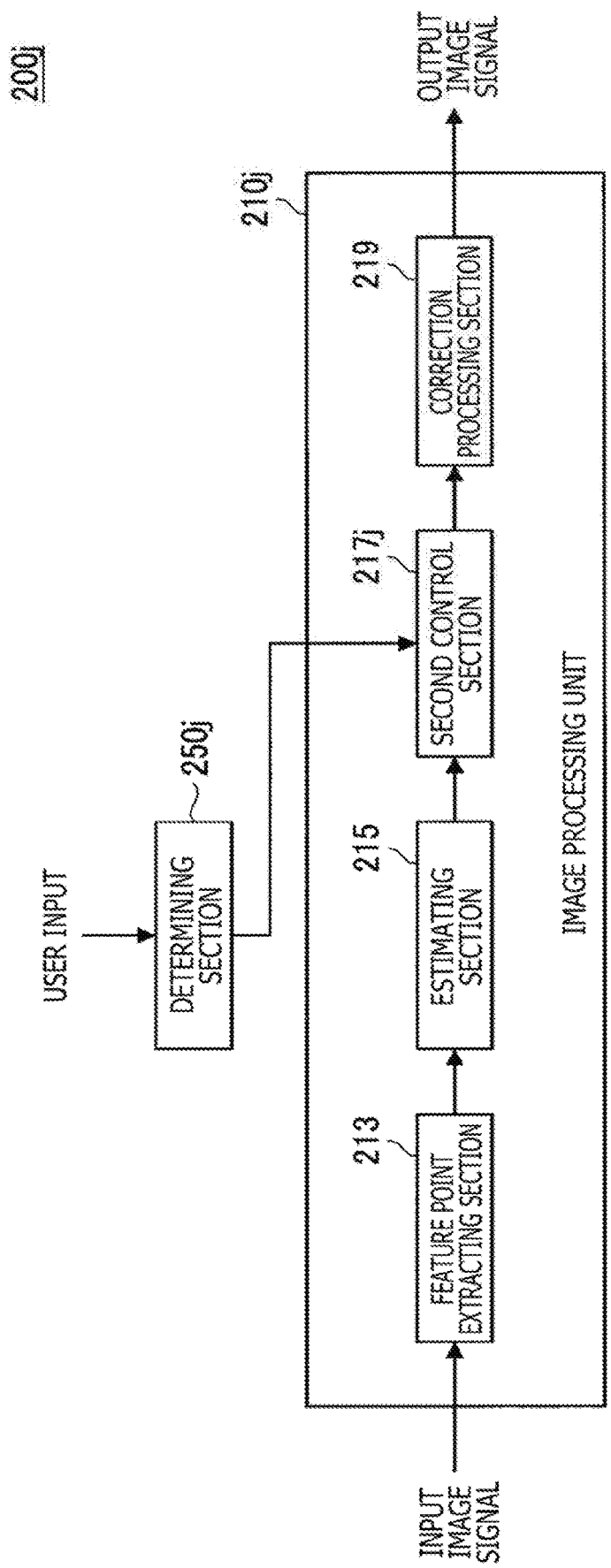
FIG. 24 is a descriptive diagram illustrating an example of control related to correction of image blurring performed by a control apparatus according to Example 10.
Figure 25:
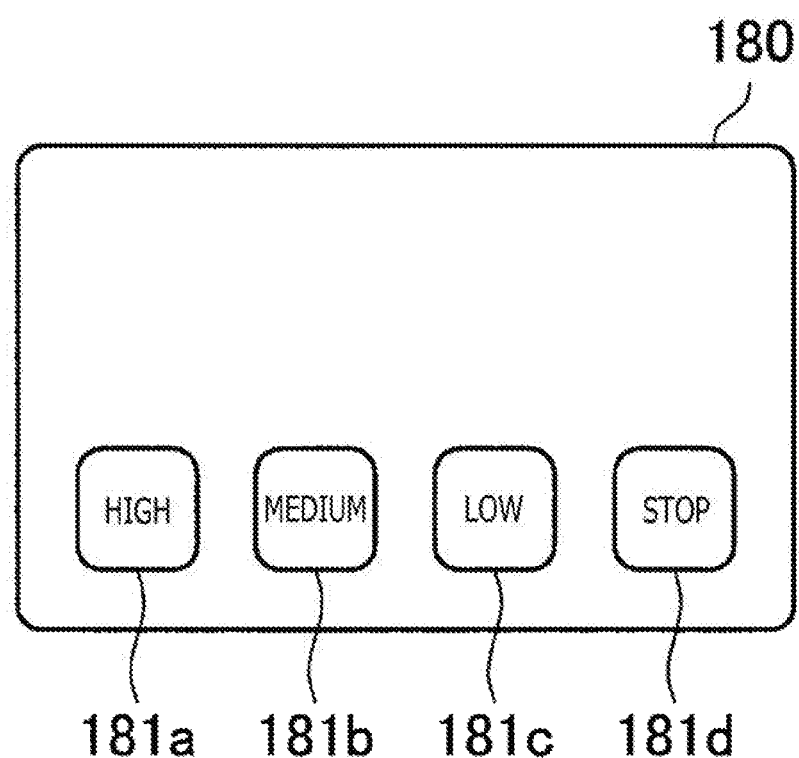
FIG. 25 is a descriptive diagram illustrating an example of control related to correction of image blurring performed by a control apparatus according to Example 10.

Now, with reference to FIGS. 24 and 25, Example 10 will be described that is an example of control using an user input as input information and related to correction of image blurring according to the user input. FIG. 24 and FIG. 25 are descriptive diagrams illustrating an example of control related to correction of image blurring performed by a control apparatus according to Example 10. Note that, in this description, the control apparatus according to the present example may be referred to as a "control apparatus 200$j$" so as to be distinguished from control apparatuses according to the other examples.

For example, FIG. 24 illustrates an example of a functional configuration of the control apparatus 200$j$ according to Example 10. Note that a precondition for the present example is that image blurring is to be corrected. Thus, in the control apparatus 200$j$, an image processing unit 210$j$ includes no component corresponding to the first control section 211 described above with reference to FIG. 3. Additionally, the control apparatus 200$j$ differs from the control apparatus 200 described with reference to FIG. 3 mainly in the operation of each of a determining section 250$j$, and a second control section 217$j$ of the image processing unit 210$j$. Thus, for operations of the control apparatus 200$j$, FIG. 3 will be described with focus on sections different from the corresponding sections of the control apparatus 200. Sections of the control apparatus 200$j$ that are substantially similar to the corresponding sections of the control apparatus 200 will not be described below in detail.

In the present example, an example will be described in which the correction intensity of the blurring correction is controlled in accordance with an instruction from the user based on an operation via a predetermined input section. That is, the determining section 250$j$ acquires a user input via the predetermined input section as input information, and determines a coefficient for controlling the degree of application of the blurring correction (that is, the correction intensity) in accordance with the acquired input information (that is, the user input). That is, the second control section 217$h$ determines a correction coefficient indicative of the correction intensity of the blurring correction on the basis of the result of the determination made by the determining section 250$h$ according to the user input.

For example, FIG. 25 illustrates an example of an input interface 180 provided in the camera head or the like. In the example illustrated in FIG. 25, buttons 181$a$ to 181$c$ are provided to specify the correction intensity of the blurring correction, and a button 181$d$ is provided to specify disabling of the blurring correction. Additionally, in the example illustrated in FIG. 25, to enable the blurring correction, any of the buttons 181$a$ to 181$c$ can be operated to selectively switch the correction intensity of the blurring correction among three stages "high," "medium," and "low."

With reference to FIG. 24 and FIG. 25, the example of the control has been described that uses the user input as input information and that is related to the correction of image blurring in accordance with the user input.

Example 11: Control According to CCU/Switching of Light Source Mode

Figure 26:
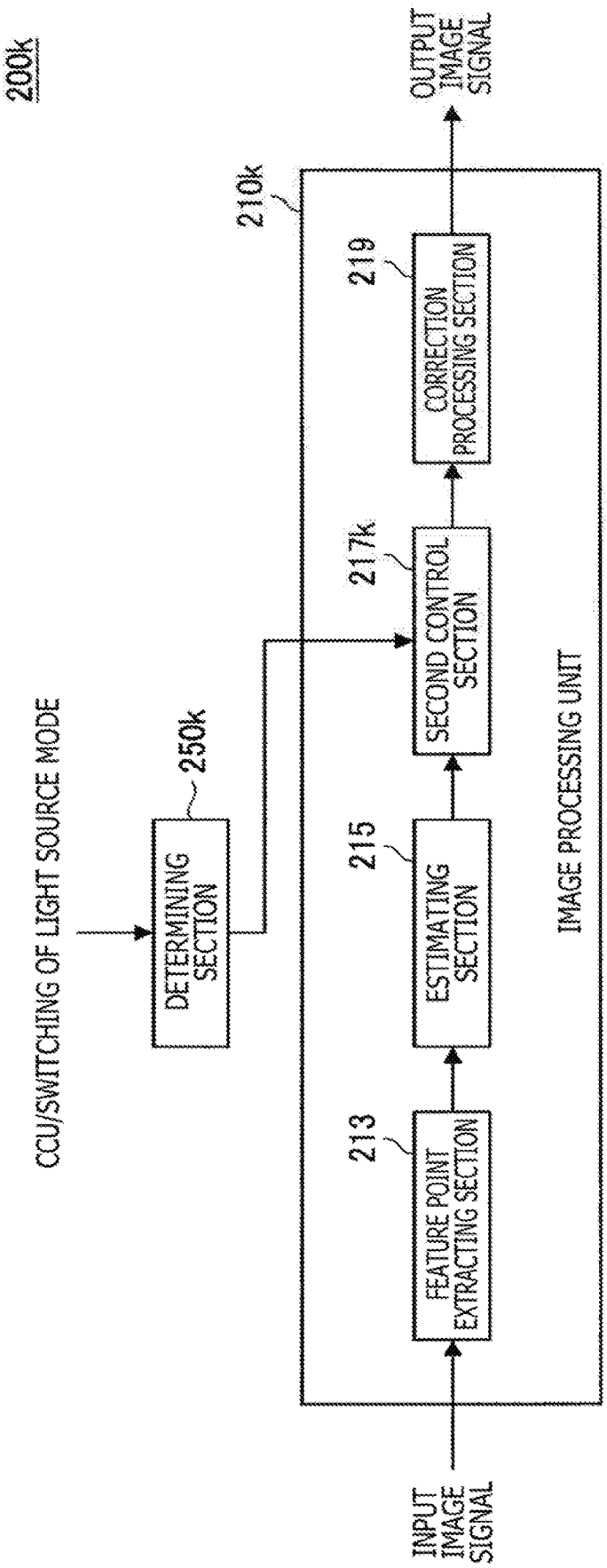
FIG. 26 is a descriptive diagram illustrating an example of control related to correction of image blurring performed by a control apparatus according to Example 11.

Now, with reference to FIG. 26, Example 11 will be described that is an example of control using, as input information, information indicative of the CCU/switching of the light source mode and related to correction of image blurring according to the switching. FIG. 26 is a descriptive diagram illustrating an example of control related to correction of image blurring performed by a control apparatus according to Example 11. Note that, in this description, the control apparatus according to the present example may be referred to as a "control apparatus 200$k$" so as to be distinguished from control apparatuses according to the other examples.

For example, FIG. 26 illustrates an example of a functional configuration of the control apparatus 200$k$ according to Example 11. Note that a precondition for the present example is that image blurring is to be corrected. Thus, in the control apparatus 200$k$, an image processing unit 210$k$ includes no component corresponding to the first control section 211 described above with reference to FIG. 3. Additionally, the control apparatus 200$k$ differs from the control apparatus 200 described with reference to FIG. 3 mainly in the operation of each of a determining section 250$k$, and a second control section 217$k$ of the image processing unit 210$k$. Thus, for operations of the control apparatus 200$k$, FIG. 3 will be described with focus on sections different from the corresponding sections of the control apparatus 200. Sections of the control apparatus 200$k$ that are substantially similar to the corresponding sections of the control apparatus 200 will not be described below in detail.

For example, temporary vibration may be caused by an operation on the CCU (for example, changing the zoom magnification), an operation of switching the light source mode, or the like, resulting in temporary image blurring. When the blurring correction is applied even in such a case, the observation target such as the living organism may become difficult to observe. In light of such circumstances, in the present example, in a case where a predetermined operation such as the operation on the CCU or the operation of switching the light source mode is detected, the control apparatus 200k provides control to temporarily reduce the correction intensity of the blurring correction or temporarily disables the blurring correction.

That is, the determining section 250k acquires, as input information, the information indicative of a detection result for the operation on the CCU, the operation of switching the light source mode, or the like, and determines a coefficient for controlling the degree of application of the blurring correction (that is, the correction intensity) in accordance with the acquired input information (that is, the information indicative of the detection result for the operation on the CCU, the operation of switching the light source mode, or the like). That is, the second control section 217h determines a correction coefficient indicative of the correction intensity of the blurring correction on the basis of the result of the determination made by the determining section 250h according to the detection result for the operation on the CCU, the operation of switching the light source mode, or the like.

Note that, in a case of having provided control to temporarily reduce the correction intensity of the blurring correction or having temporarily disabled the blurring correction, the control apparatus 200k may return, after elapse of a given time, the correction intensity of the blurring correction to a state before the control.

With reference to FIG. 26, Example 11 has been described, which is an example of the control using, as input information, the information indicative of the CCU/switching of the light source mode and related to the correction of image blurring according to the switching.

Example 12: Control According to Calculation Result for Motion Vectors

Figure 27:
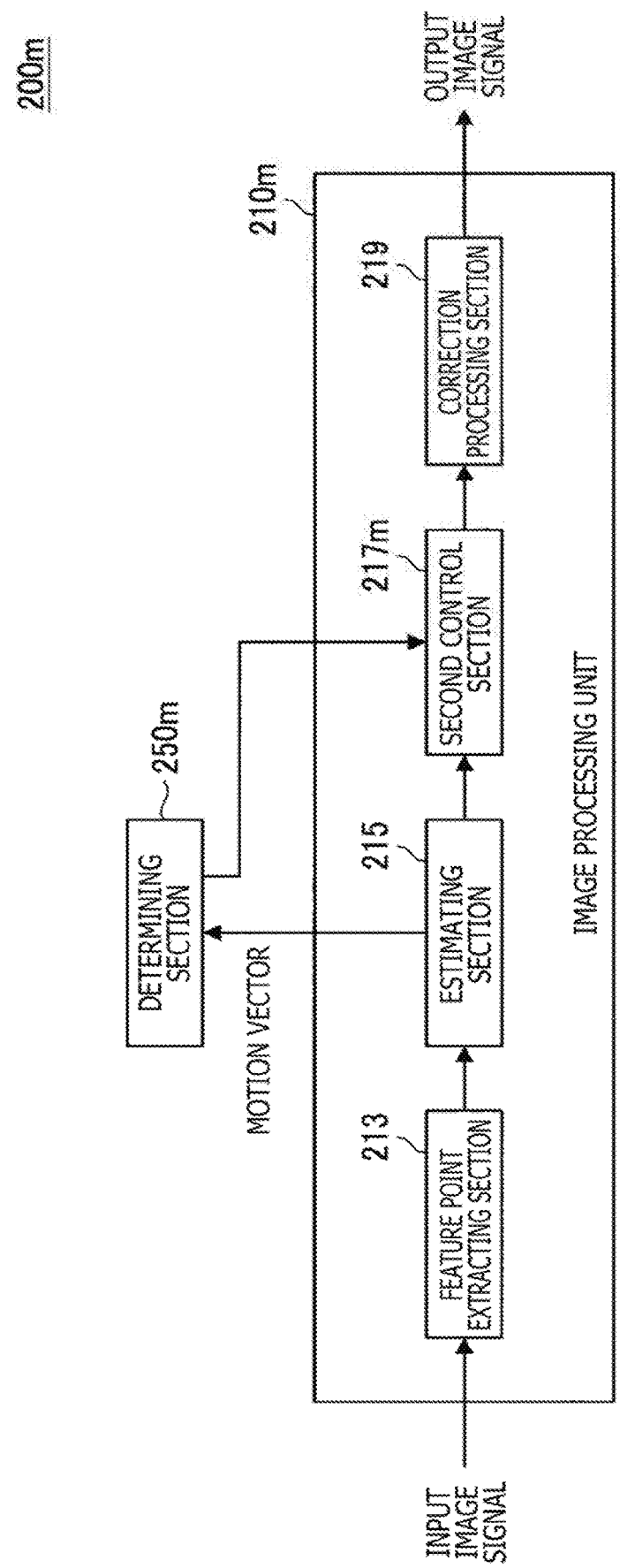
FIG. 27 is a descriptive diagram illustrating an example of control related to correction of image blurring performed by a control apparatus according to Example 12.

Now, with reference to FIG. 27, Example 12 will be described that is an example of control using, as input information, information indicative of a calculation result for motion vectors and related to correction of image blurring according to the calculation result for the motion vectors. FIG. 27 is a descriptive diagram illustrating an example of control related to correction of image blurring performed by a control apparatus according to Example 12. Note that, in this description, the control apparatus according to the present example may be referred to as a "control apparatus 200m" so as to be distinguished from control apparatuses according to the other examples.

For example, FIG. 27 illustrates an example of a functional configuration of the control apparatus 200m according to Example 12. Note that a precondition for the present example is that image blurring is to be corrected. Thus, in the control apparatus 200m, an image processing unit 210m includes no component corresponding to the first control section 211 described above with reference to FIG. 3. Additionally, the control apparatus 200m differs from the control apparatus 200 described with reference to FIG. 3 mainly in the operation of each of a determining section 250m, and a second control section 217m of the image processing unit 210m. Thus, for operations of the control apparatus 200m, FIG. 3 will be described with focus on sections different from the corresponding sections of the control apparatus 200. Sections of the control apparatus 200m that are substantially similar to the corresponding sections of the control apparatus 200 will not be described below in detail.

The determining section 250m acquires, as input information, the information indicative of the result of estimation of motion vectors performed by the estimating section 215, and determines a coefficient for controlling the degree of application of the blurring correction (that is, the correction intensity) in accordance with the acquired input information (that is, the information indicative of the estimation result for the motion vectors). That is, the second control section 217m determines a correction coefficient indicative of the correction intensity of the blurring correction on the basis of the result of the determination made by the determining section 250m according to the estimation result for the motion vectors.

By way of a specific example, in a case where a predetermined operation is performed such as an operation of translating the imaging section as in insertion of the endoscope or what is called a pan operation, the position or orientation of the imaging section is changed in conjunction with the operation, and the change is detected as a motion vector. In a case where such an intentional operation is performed, when the blurring correction is applied even to motion of the image involved in the operation, the observation target such as the living organism may become difficult to observe. Thus, for example, in a case where the estimation of the motion vectors is recognized to result from a change in the position or orientation of the imaging section by the intentional operation, the observation target such as the living organism may be made easier to observe by providing control to reduce the correction intensity or temporarily disabling the blurring correction.

Note that a method for recognizing that the estimation of the motion vectors results from a change in the position or orientation of the imaging section by an intentional operation is not particularly limited as long as the recognition can be achieved. For example, when the endoscope is inserted or in a case where a pan operation is performed, the entire image may change steadily in a given direction. In such a case, for example, the estimation result for the motion vectors tends to indicate a substantially equal direction among a plurality of frames and the magnitude of each motion vector tends to vary slowly. Such properties can be utilized in the following manner: for example, in a case where a change in the entire image is recognized to be a steady change in a given direction instead of an instantaneous change, the position or orientation of the imaging section can be recognized to have been changed by an intentional operation as in the insertion of the endoscope, the pan operation, or the like.

With reference to FIG. 27, Example 12 has been described, which is an example of the control using, as input information, the information indicative of the calculation result for the motion vectors and related to the correction of image blurring according to the calculation result for the motion vectors.

Example 13: Control According to Detection Status of AF/AE

Figure 28:
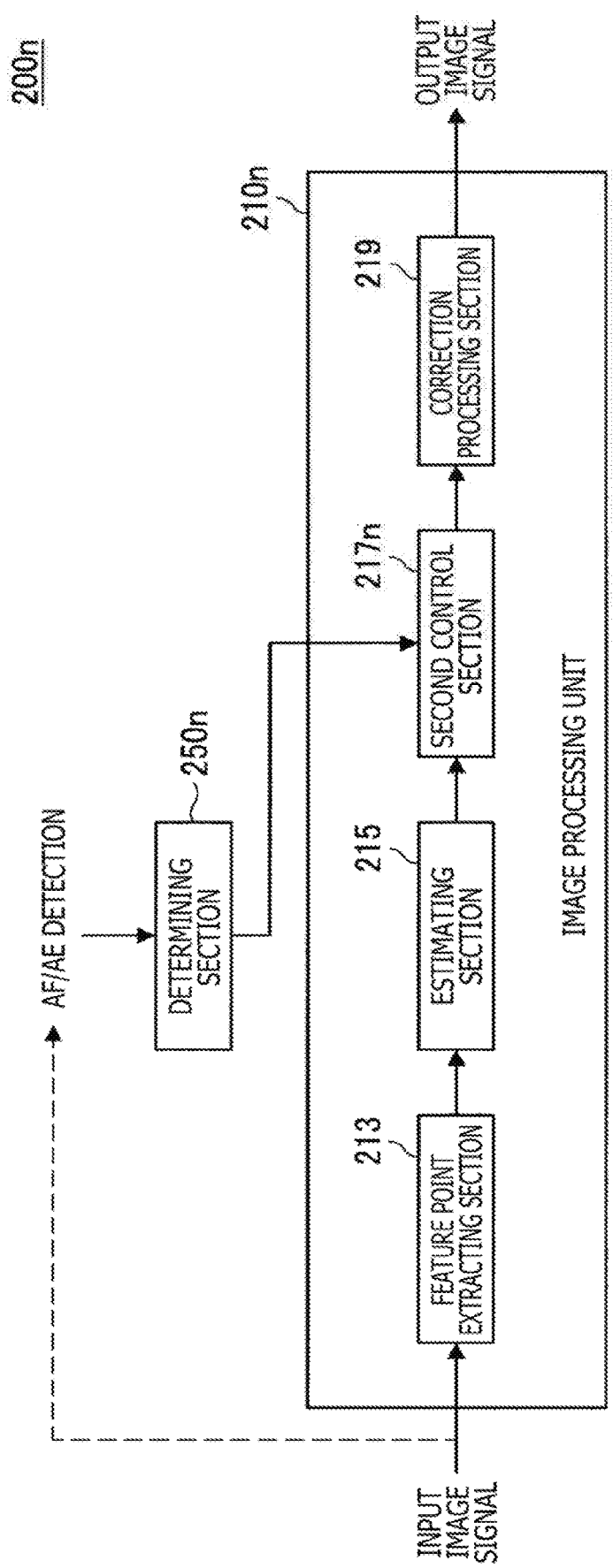
FIG. 28 is a descriptive diagram illustrating an example of control related to correction of image blurring performed by a control apparatus according to Example 13.

Now, with reference to FIG. 28, Example 13 will be described that is an example of control using, as input information, information indicative of a detection status of AF (Autofocus)/AE (Automatic Exposure) and related to correction of image blurring according to the detection status of the AF/AE. FIG. 28 is a descriptive diagram illustrating an example of control related to correction of image blurring performed by a control apparatus according to Example 13. Note that, in this description, the control apparatus according to the present example may be referred to as a "control apparatus 200n" so as to be distinguished from control apparatuses according to the other examples.

For example, FIG. 28 illustrates an example of a functional configuration of the control apparatus 200n according to Example 13. Note that a precondition for the present example is that image blurring is to be corrected. Thus, in the control apparatus 200n, an image processing unit 210n includes no component corresponding to the first control section 211 described above with reference to FIG. 3. Additionally, the control apparatus 200n differs from the control apparatus 200 described with reference to FIG. 3 mainly in the operation of each of a determining section 250n, and a second control section 217n of the image processing unit 210n. Thus, for operations of the control apparatus 200n, FIG. 3 will be described with focus on sections different from the corresponding sections of the control apparatus 200. Sections of the control apparatus 200n that are substantially similar to the corresponding sections of the control apparatus 200 will not be described below in detail.

The determining section 250n acquires, as input information, the information indicative of the detection status of AF or AE, and determines a coefficient for controlling the degree of application of the blurring correction (that is, the correction intensity) in accordance with the acquired input information (that is, the information indicative of the detection status of AF or AE). That is, the second control section 217n determines a correction coefficient indicative of the correction intensity of the blurring correction on the basis of the result of the determination made by the determining section 250n according to the detection status of AF or AE. Note that a method for recognizing the detection status of AF or AE is not particularly limited as long as the recognition can be achieved. By way of example of another example, information indicating the detection status of AF or AE from an image sensor or the like provided in the imaging section may be acquired from the imaging section (or the image sensor itself). Additionally, by way of another example, the detection status of AF or AE may be estimated by analyzing the captured image.

Specifically, a failure in the detection of AF or AE may prevent correct extraction of feature points or correct estimation of motion vectors based on the result of extraction of the feature points, resulting in reduced reliability of the correction value for the blurring correction. By way of a more specific example, a failure in AF leads to blurring of the image, making extraction of feature points such as edges difficult. Additionally, in a case where a failure in AF results in reduced lightness of the entire image, extracting feature points is difficult.

It is assumed that, in a case where the correction intensity of the blurring correction is increased with the reliability of the correction value for the blurring correction reduced as described above, the blurring correction fails to be applied in an appropriate manner, making the observation target such as the living organism difficult to observe. Thus, for example, in a case where the detection of AF or Ae fails, the observation target such as the living organism can be prevented from becoming difficult to observe by reducing the correction intensity of the blurring correction or temporarily disabling the blurring correction.

With reference to FIG. 28, Example 13 has been described, which is an example of the control using, as input information, the information indicative of the detection status of AF (Autofocus)/AE (Automatic Exposure) and related to the correction of image blurring according to the detection status of AF/AE.

Example 14: Control According to Detection Result for Lens Stain

Figure 29:
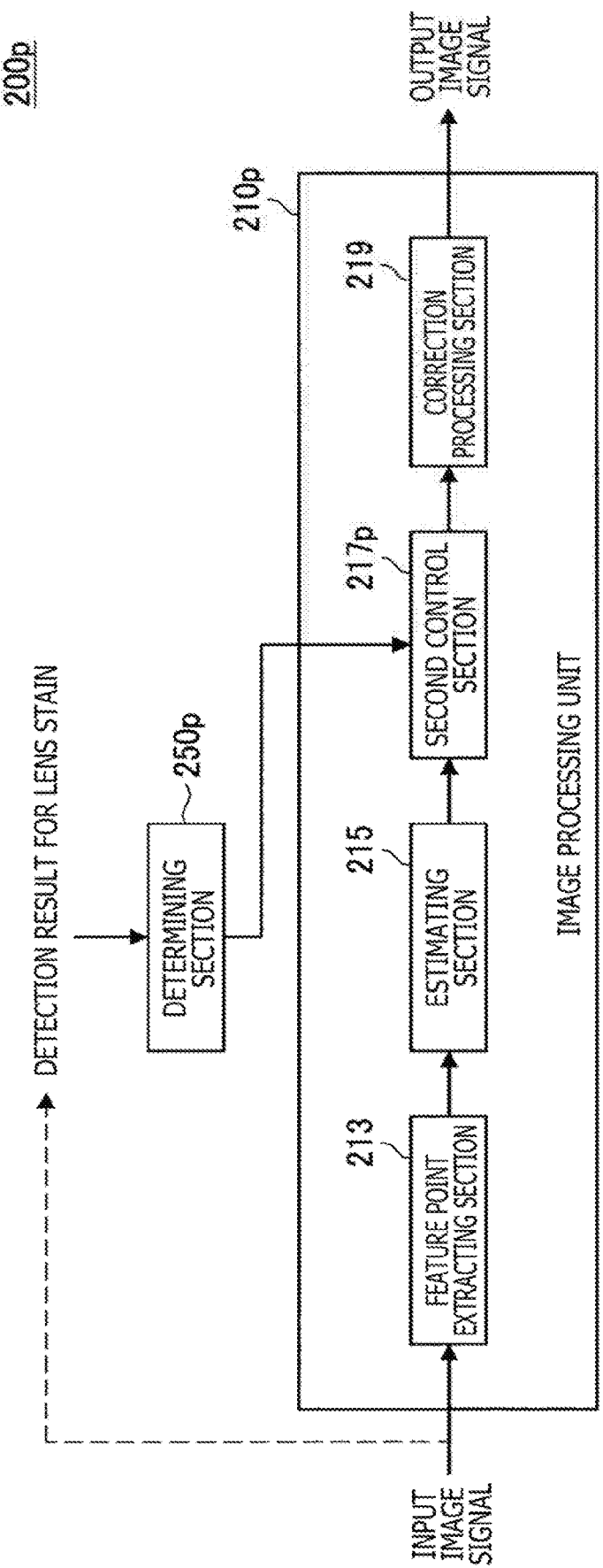
FIG. 29 is a descriptive diagram illustrating an example of control related to correction of image blurring performed by a control apparatus according to Example 14.

Now, with reference to FIG. 29, Example 14 will be described that is an example of control using, as input information, information indicative of a detection result for lens stain and related to correction of image blurring according to the detection result for lens stain. FIG. 29 is a descriptive diagram illustrating an example of control related to correction of image blurring performed by a control apparatus according to Example 14. Note that, in this description, the control apparatus according to the present example may be referred to as a "control apparatus 200p" so as to be distinguished from control apparatuses according to the other examples.

For example, FIG. 29 illustrates an example of a functional configuration of the control apparatus 200p according to Example 14. Note that a precondition for the present example is that image blurring is to be corrected. Thus, in the control apparatus 200p, an image processing unit 210p includes no component corresponding to the first control section 211 described above with reference to FIG. 3. Additionally, the control apparatus 200p differs from the control apparatus 200 described with reference to FIG. 3 mainly in the operation of each of a determining section 250p, and a second control section 217p of the image processing unit 210p. Thus, for operations of the control apparatus 200p, FIG. 3 will be described with focus on sections different from the corresponding sections of the control apparatus 200. Sections of the control apparatus 200p that are substantially similar to the corresponding sections of the control apparatus 200 will not be described below in detail.

The determining section 250p acquires, as input information, the information indicative of the detection result for lens stain, and determines a coefficient for controlling the degree of application of the blurring correction (that is, the correction intensity) in accordance with the acquired input information (that is, the information indicative of the detection result for lens stain). That is, the second control section 217p determines a correction coefficient indicative of the correction intensity of the blurring correction on the basis of the result of the determination made by the determining section 250p according to the detection result for lens stain. Note that a method for detecting lens stain is not particularly limited as long as the method allows lens stain to be detected. For example, lens stain may be detected by various sensors or the like. Additionally, by way of another example, lens stain may be detected by analyzing the captured image.

Specifically, under circumstances where the lens is stained, the stain may shield a subject corresponding to the observation target such as the living organism or blur the image. Under such circumstances, feature points may be prevented from being correctly extracted or motion vectors may be prevented from being correctly estimated on the basis of the result of extraction of the feature points, resulting in reduced reliability of the correction value for the blurring correction.

It is assumed that, in a case where the correction intensity of the blurring correction is increased with the reliability of the correction value for the blurring correction reduced as described above, the blurring correction fails to be applied in an appropriate manner, making the observation target such as the living organism difficult to observe. Thus, for example, in a case where stain attached to the lens is detected, the observation target such as the living organism can be prevented from becoming difficult to observe by reducing the correction intensity of the blurring correction or temporarily disabling the blurring correction.

With reference to FIG. 29, Example 14 has been described, which is an example of the control using, as input information, the information indicative of the detection result for lens stain and related to the correction of image blurring according to the detection result for lens stain.

Example 15: Control According to Detection Result for Smoke or Mist

Figure 30:
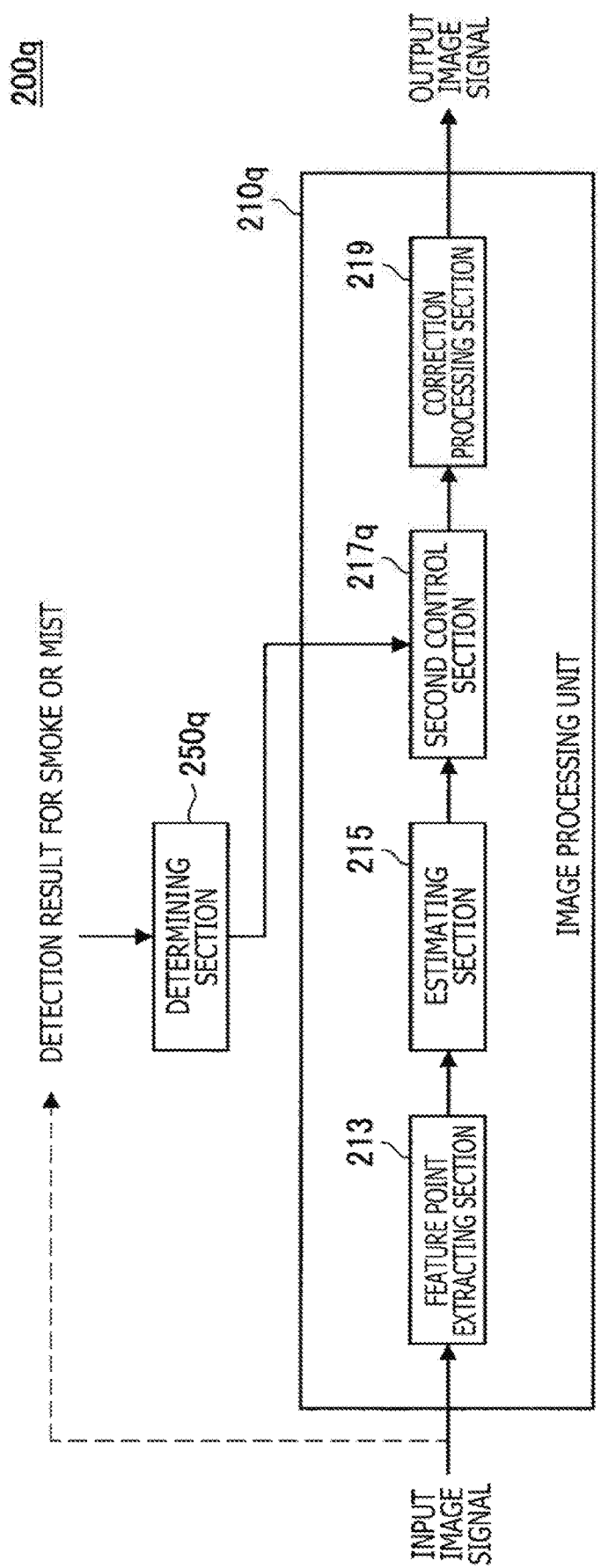
FIG. 30 is a descriptive diagram illustrating an example of control related to correction of image blurring performed by a control apparatus according to Example 15.

Now, with reference to FIG. 30, Example 15 will be described that is an example of control using, as input information, information indicative of a detection result for smoke or mist and related to correction of image blurring according to the detection result for smoke or mist. FIG. 30 is a descriptive diagram illustrating an example of control related to correction of image blurring performed by a control apparatus according to Example 15. Note that, in this description, the control apparatus according to the present example may be referred to as a "control apparatus $200q$" so as to be distinguished from control apparatuses according to the other examples.

For example, FIG. 30 illustrates an example of a functional configuration of the control apparatus $200q$ according to Example 15. Note that a precondition for the present example is that image blurring is to be corrected. Thus, in the control apparatus $200q$, an image processing unit $210q$ includes no component corresponding to the first control section 211 described above with reference to FIG. 3. Additionally, the control apparatus $200q$ differs from the control apparatus 200 described with reference to FIG. 3 mainly in the operation of each of a determining section $250q$, and a second control section $217q$ of the image processing unit $210q$. Thus, for operations of the control apparatus $200q$, FIG. 3 will be described with focus on sections different from the corresponding sections of the control apparatus 200. Sections of the control apparatus $200q$ that are substantially similar to the corresponding sections of the control apparatus 200 will not be described below in detail.

Specifically, it is assumed that mist caused by spraying of a drug or the like temporarily shields a subject corresponding to the observation target such as the living organism. It is also assumed that smoke caused by the use of an energy device or the like temporarily shields a subject corresponding to the observation target such as the living organism. Under circumstances where a visible gaseous substance such as smoke or mist thus temporarily shields a subject corresponding to the observation target such as the living organism, feature points may be prevented from being correctly extracted or motion vectors may be prevented from being correctly estimated on the basis of the result of extraction of the feature points, resulting in reduced reliability of the correction value for the blurring correction. It is assumed that, in a case where the correction intensity of the blurring correction is increased with the reliability of the correction value for the blurring correction reduced as described above, the blurring correction fails to be applied in an appropriate manner, making the observation target such as the living organism difficult to observe.

The determining section $250q$ may acquire, as input information, the information indicative of the detection result for smoke, mist, or the like, and determine a coefficient for controlling the degree of application of the blurring correction (that is, the correction intensity) in accordance with the acquired input information (that is, the information indicative of the detection result for the gaseous substance). That is, the second control section $217p$ determines a correction coefficient indicative of the correction intensity of the blurring correction on the basis of the result of the determination made by the determining section $250p$ according to the detection result for a visible gaseous substance such as smoke or mist. Note that a method for detecting a visible gaseous substance such as smoke or mist is not particularly limited as long as the method allows the visible gaseous substance to be detected. For example, the gaseous substance may be detected by various sensors or the like. Additionally, by way of another example, the gaseous substance may be detected by analyzing the captured image.

Thus, for example, in a case where the visible gaseous substance such as smoke or mist is detected, the observation target such as the living organism can be prevented from becoming difficult to observe by reducing the correction intensity of the blurring correction or temporarily disabling the blurring correction. Note that, on the basis of a concept similar to the concept of Example 5 described above, the correction intensity of the blurring correction may be controlled according to the ratio of a part of the subject corresponding to the observation target such as the living organism which part is shielded, in the screen, by the visible gaseous substance such as smoke or mist.

With reference to FIG. 30, Example 15 has been described, which is an example of the control using, as input information, the information indicative of the detection result for smoke or mist and related to the correction of image blurring according to the detection result for smoke or mist.

Example 16: Example of Control According to Procedure

Now, Example 16 will be described that is an example in which each of the above-described examples is appropriately applied according to a procedure, a correction target, a technique, or the like in surgery or the like.

By way of a specific example, an operation in gastrointestinal surgery is assumed, and procedures are assumed to be executed in the order of "incision and exfoliation," "biopsy," and "blood vessel treatment." In such a case, for example, in the "incision and exfoliation" procedure, whether or not to apply the blurring correction or the correction intensity of the blurring correction may be controlled according to at least any one of the types of input information such as the occupancy of a surgical instrument in the screen, the state of the surgical instrument, or the detection result for smoke or mist. Additionally, in the "biopsy" procedure, whether or not to apply the blurring correction or the correction intensity of the blurring correction may be controlled according to at least any one of the types of input information such as the occupancy of a surgical instrument in the screen and the state of the surgical instrument. Additionally, in the "blood vessel treatment" procedure, whether or not to apply the blurring correction or the correction intensity of the blurring correction may be controlled according to at least any one of the types of input information such as the zoom magnification, the working distance, and the detection result for lens stain.

Additionally, for lengthy surgery, whether or not to apply the blurring correction or the correction intensity of the blurring correction may be controlled, for example, according to the operative duration. Additionally, under circumstances where the operator moves, whether or not to apply the blurring correction or the correction intensity of the blurring correction may be controlled, for example, according to the distance between the operator and the monitor.

Note that the coefficient for controlling the correction intensity of the blurring correction may be calculated in accordance with a plurality of types of input information. In such a case, for example, the coefficients corresponding to the respective types of input information may be multiplied together to calculate a coefficient to be finally applied. Additionally, the coefficients corresponding to the respective types of input information may be weighted according to a utilization scene.

Example 16 has been described that is an example in which each of the above-described examples is appropriately applied according to the procedure, the correction target, the technique, or the like in the surgery or the like.

3. Applied Example

Now, as an applied example of a medical observation system according to the embodiment of the present disclosure, an example of the medical observation system configured as a microscopic imaging system including a microscope unit will be described with reference to FIG. 31.

Figure 31:
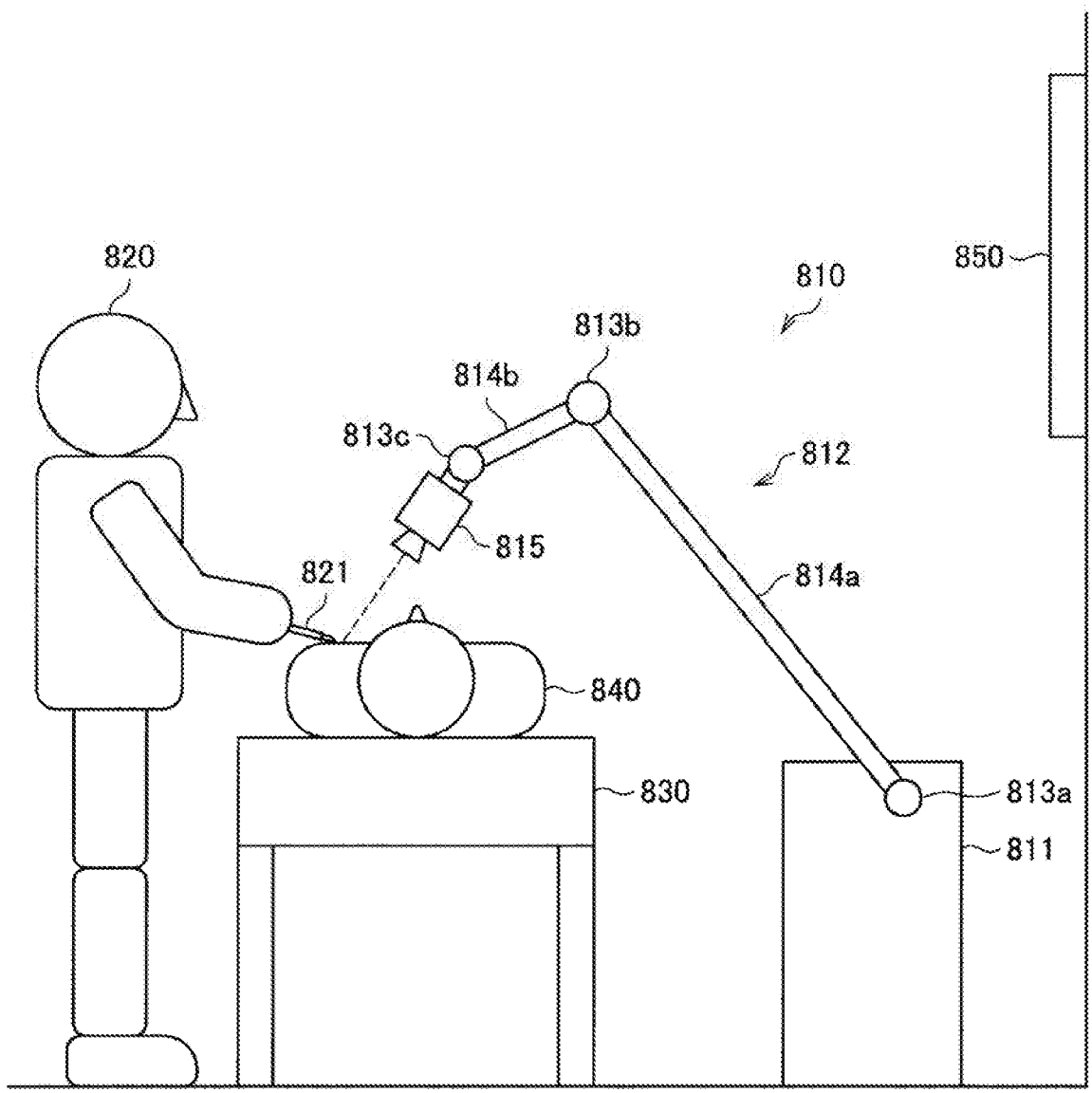
FIG. 31 is a descriptive diagram illustrating an applied example of a medical observation system according to the embodiment of the present disclosure.

FIG. 31 is a descriptive diagram illustrating the applied example of the medical observation system according to the embodiment of the present disclosure and also illustrating an example of a general configuration of the microscopic imaging system. Specifically, FIG. 31 illustrates an example of the use of a surgical video microscope apparatus including an arm, as an applied example of the use of the medical observation system according to the embodiment of the present disclosure.

For example, FIG. 31 schematically illustrates the manner of medical treatment using the surgical video microscope apparatus. Specifically, FIG. 31 illustrates that a surgeon who is an operator (user) 820 is operating on a medical treatment target (patient) 840 on an operating table 830 using a surgical instrument 821, for example, a scalpel, tweezers, or forceps. In the following description, the medical treatment is intended to be a general term for various medical treatments such as surgery and examinations executed on the patient, who is the medical treatment target 840, by the surgeon, who is the user 820. Additionally, in the example illustrated in FIG. 31, the manner of surgery is illustrated as an example of medical treatment. However, the medical treatment using the surgical video microscope apparatus 810 is not limited to surgery but may be any of various other medical treatments.

The surgical video microscope apparatus 810 is provided beside the operating table 830. The surgical video microscope apparatus 810 includes a base section 811 corresponding to a base, an arm section 812 extending from the base section 811, and an imaging unit 815 connected to a distal end of the arm section 812 as a distal-end unit. The arm section 812 includes a plurality of joint sections 813*a*, 813*b*, and 813*c*, a plurality of links 814*a* and 814*b* coupled together by the joint sections 813*a* and 813*b*, and an imaging unit 815 provided at a distal end of the arm section 812. In the example illustrated in FIG. 31, the arm section 812 includes the three joint sections 813*a* to 813*c* and the two links 814*a* and 814*b* for simplification. However, in actuality, the numbers and shapes of the joint sections 813*a* to 813*c* and the links 814*a* and 814*b*, the directions of driving shafts of the joint sections 813*a* to 813*c*, and the like may be appropriately set so as to achieve a desired degree of freedom with the degrees of freedom of positions and postures of the arm section 812 and the imaging unit 815 taken into account.

The joint sections 813*a* to 813*c* have a function to pivotally couple the links 814*a* and 814*b* together, and are rotationally driven to control driving of the arm section 812. Here, in the description below, the position of each component of the surgical video microscope apparatus 810 means a position (coordinates) in a space defined for driving control. The posture of each component means the orientation (angle) with respect to an optional axis in the space defined for driving control. Additionally, in the description below, driving (or driving control) of the arm section 812 refers to a change in the position and orientation of each component of the arm section 812 effected by driving (or driving control) of the joint sections 813*a* to 813*c* and driving (or driving control) of the joint sections 813*a* to 813*c* (or refers to the control of the change in the position and posture).

The imaging unit 815 is connected to a distal end of the arm section 812 as a distal-end unit. The imaging unit 815 is a unit that acquires an image of an imaging target, for example, a camera capable of capturing moving images or still images. As illustrated in FIG. 31, to allow the imaging unit 815 provided at the distal end of the arm section 812 to image a medical treatment site of the medical treatment target 840, the surgical video microscope apparatus 810 controls the postures and positions of the arm section 812 and the imaging unit 815. Note that the configuration of the imaging unit 815 connected to the distal end of the arm section 812 as a distal-end unit is not particularly limited and that, for example, the imaging unit 815 is configured as a microscope that acquires an enlarged image of the imaging target. Additionally, the imaging unit 815 may be configured such that the imaging unit 815 can be installed on and removed from the arm section 812. In such a configuration, for example, the imaging unit 815 corresponding to an intended use may be appropriately connected to the distal end of the arm section 812 as a distal-end unit. Note that, as the imaging unit 815, for example, an imaging apparatus can be applied to which a branching optical system according to the above-described embodiment is applied. Additionally, this description focuses on the application of the imaging unit 815 as a distal-end unit. However, the distal-end unit connected to the distal end of the arm section 812 is not necessarily limited to the imaging unit 815.

Additionally, a display apparatus 850 such as a monitor or a display is installed at a position opposite to the user 820. An image of the medical treatment site captured by the imaging unit 815 is displayed on a display screen of the display apparatus 850 as an electronic image. The user 820 executes various treatments while viewing the electronic image of the medical treatment site displayed on the display screen of the display apparatus 850.

The configuration described above allows surgery to be performed with the medical treatment site being imaged by the surgical video microscope apparatus 810.

4. Example of Hardware Configuration

Figure 32:
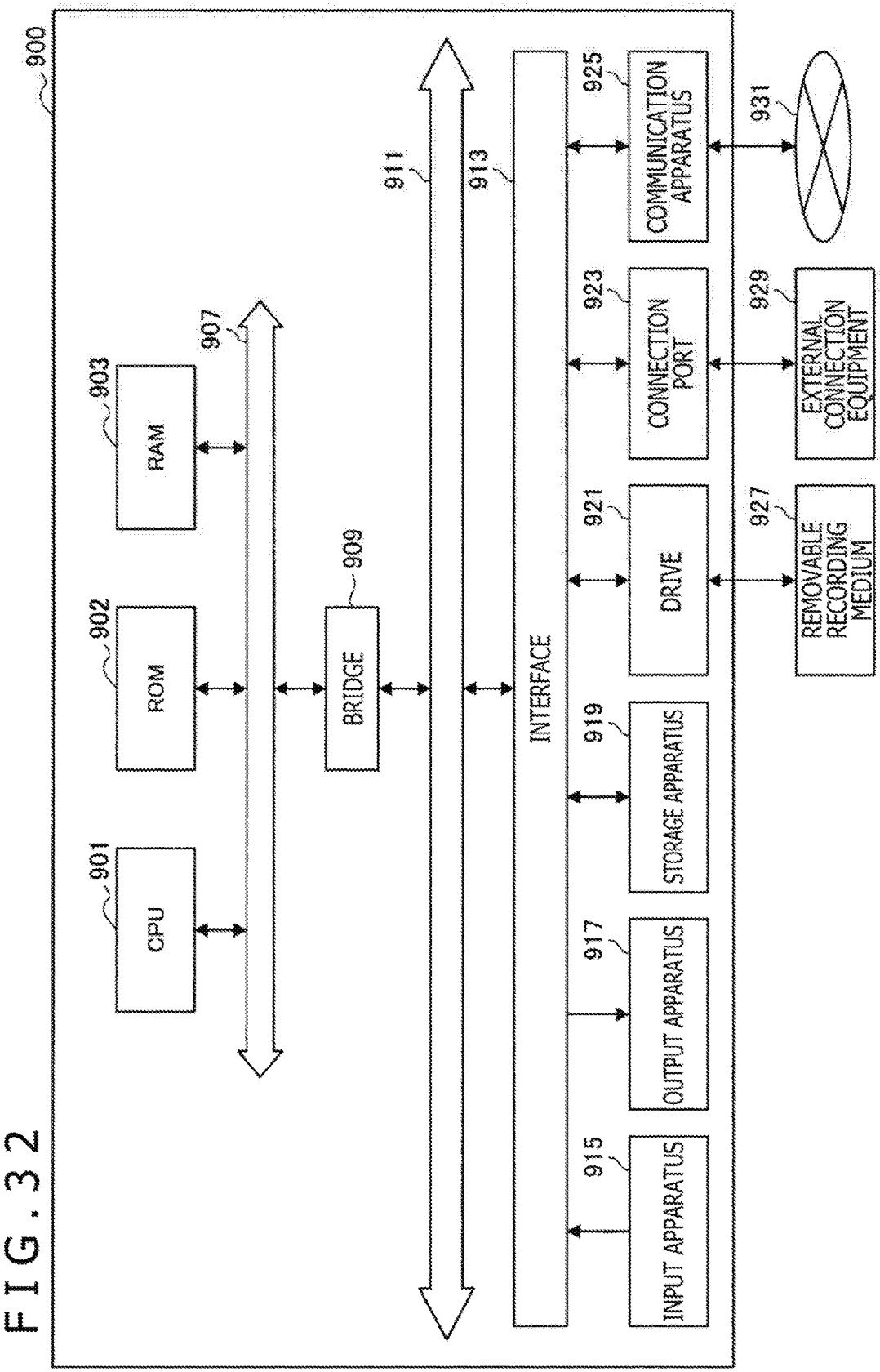
FIG. 32 is a functional block diagram illustrating a configuration example of a hardware configuration of an information processing apparatus constituting a medical observation system according to the embodiment of the present disclosure.

Now, with reference to FIG. 32, an example of a hardware configuration of what is called an information processing apparatus executing various types of processing, such as the CCU in the above-described endoscopic surgery system. FIG. 32 is a functional block diagram illustrating a configuration example of a hardware configuration of an information processing apparatus constituting a medical observation system according to the embodiment of the present disclosure.

An information processing apparatus 900 constituting the medical observation system according to the present embodiment mainly includes a CPU 901, a ROM 902, and a RAM 903. Additionally, the information processing apparatus 900 further includes a host bus 907, a bridge 909, an external bus 911, an interface 913, an input apparatus 915, an output apparatus 917, a storage apparatus 919, a drive 921, a connection port 923, and a communication apparatus 925.

The CPU 901 functions as an arithmetic processing apparatus and a control apparatus to control operations in general in the information processing apparatus 900 or some of the operations in accordance with various programs recorded in the ROM 902, the RAM 903, the storage apparatus 919, or a removable recording medium 927. The ROM 902 stores programs, arithmetic parameters, and the like used by the CPU 901. The RAM 903 primarily stores programs used by the CPU 901, and for example, parameters appropriately varying during execution of the programs. The above-described components are connected together by the host bus 907 including an internal bus such as a CPU bus. For example, the image processing unit 210 and the determining section 250 described with reference to FIG. 3 may include the CPU 901.

The host bus 907 is connected to the external bus 911 such as a PCI (Peripheral Component Interconnect/Interface) bus via the bridge 909. Additionally, the external bus 911 connects to the input apparatus 915, the output apparatus 917, the storage apparatus 919, the drive 921, the connection port 923, and the communication apparatus 925 via the interface 913.

The input apparatus 915 is operating means operated by the user, such as a mouse, a keyboard, a touch panel, a button, a switch, a lever, and a pedal. The input apparatus 915 may also be remote control means (what is called a remote controller) utilizing infrared rays or other radio waves, or external connection equipment 929 such as a cellular phone or a PDA supporting operation of the information processing apparatus 900. The input apparatus 915 includes, for example, an input control circuit that generates an input signal based on information input by the user using the above-described operating means and that outputs the input signal to the CPU 901. By operating the input apparatus 915, the user of the information processing apparatus 900 can input various data to the information processing apparatus 900 and provide the information processing apparatus 900 with instructions to perform processing operations.

The output apparatus 917 includes an apparatus capable of visually or auditorily notifying the user of acquired information. Examples of such an apparatus include display apparatuses such as a CRT display apparatus, a liquid crystal display apparatus, a plasma display apparatus, an EL display apparatus, and a lamp, sound output apparatuses such as a speaker and a headphone, and a printer apparatus. The output apparatus 917 outputs results obtained from various types of processing executed by the information processing apparatus 900. Specifically, the display apparatus displays, in text or as images, results obtained from various types of processing executed by the information processing apparatus 900. On the other hand, the sound output apparatus converts, into an analog signal, an audio signal consisting of reproduced sound data, acoustic data, or the like, and outputs the analog signal.

The storage apparatus 919 is a apparatus for data storage configured as a part of a storage section of the information processing apparatus 900. The storage apparatus 919 includes, for example, a magnetic storage device such as an HDD (Hard Disk Drive), a semiconductor storage device, or an optical storage device or a photomagnetic storage device. The storage apparatus 919 stores programs executed by the CPU 901, various data, and the like.

The drive 921 is a reader/writer for recording media built in the information processing apparatus 900 or an external reader/writer for recording media attached to the information processing apparatus 900. The drive 921 reads information recorded in the removable recording medium 927 such as a magnetic disk, an optical disc, a photomagnetic disk, or a semiconductor memory that is mounted in the drive 921, and outputs the information to the RAM 903. Additionally, the drive 921 can write recording into the removable recording medium 927 such as a magnetic disk, an optical disc, a photomagnetic disk, or a semiconductor memory that is mounted in the drive 921. The removable recording medium 927 is, for example, a DVD medium, an HD-DVD medium, or a Blu-ray (registered trademark) medium. Additionally, the removable recording medium 927 may be a CompactFlash (registered trademark) (CF), a flash memory, an SD memory card (Secure Digital memory card), or the like. Additionally, the removable recording medium 927 may be, for example, an IC card (Integrated Circuit card) or electronic instrument in which a non-contact IC chip is mounted.

The connection port 923 is a port for direct connection to the information processing apparatus 900. An example of the connection port 923 is a USB (Universal Serial Bus) port, an IEEE 1394 port, or an SCSI (Small Computer System Interface) port. Another example of the connection port 923 is an RS-232C port, an optical audio terminal, an HDMI (registered trademark) (High-Definition Multimedia Interface) port, or the like. Connecting the external connection equipment 929 to the connection port 923 allows the information processing apparatus 900 to acquire various data directly from the external connection equipment 929 and provide various data to the external connection equipment 929.

The communication apparatus 925 is a communication interface including, for example, a communication device to be connected to a communication network (network) 931. The communication apparatus 925 is, for example, a communication card for a wired or wireless LAN (Local Area Network), Bluetooth (registered trademark), or WUSB (Wireless USB). Additionally, the communication apparatus 925 may be a router for optical communication, a router for ADSL (Asymmetric Digital Subscriber Line), a modem for various communications, or the like. The communication apparatus 925 can transmit and receive signals and the like, for example, to and from the Internet or any other communication equipment in accordance with a predetermined protocol, for example, TCP/IP. Additionally, the communication network 931 connected to the communication apparatus 925 includes a network connected by wire or wirelessly to the communication apparatus 925, and may be, for example, the Internet, a home LAN, infrared communication, radio wave communication, or satellite communication.

The example of the hardware configuration has been disclosed that can implement the functions of the information processing apparatus 900 constituting the medical observation system according to the embodiment of the present disclosure. Each of the above-described components may include a general-purpose member or hardware dedicated to the functions of the component. Accordingly, the hardware configuration can be appropriately varied according to the technique level of the moment when the present embodiment is implemented. Note that, although not illustrated in FIG. 32, the configuration, needless to say, includes various components corresponding to the information processing apparatus 900 constituting the medical observation system.

Note that a computer program can be created that is configured to realize each function of the information processing apparatus 900 constituting the medical observation system according to the present embodiment described above and that the computer program can be implemented in a personal computer or the like. Additionally, a computer-readable recording medium can be provided in which such a computer program is stored. The recording medium is, for example, a magnetic disk, an optical disc, a photomagnetic disk, or a flash memory. Additionally, the above-described computer program may be distributed, for example, via the network instead of using the recording medium. Additionally, the number of computers caused to execute the computer program is not particularly limited. For example, the computer program may be executed by a plurality of computers (for example, a plurality of servers) in cooperation.

5. Conclusion

As described above, in the medical observation system according to the present embodiment, the control apparatus 200 controls whether or not to apply correction of image blurring and the intensity of the correction in a case where the correction is applied, on the basis of the input information corresponding to various states or circumstances.

By way of a specific example, the control apparatus 200 may provide control to increase the degree of correction of image blurring consistently with zoom magnification of the imaging section such as the camera head. In other words, the control apparatus 200 may provide control to reduce the degree of correction of image blurring consistently with zoom magnification. With such a configuration, even under circumstances where blurring correction is performed on the basis of motion vectors indicative of motion of a surgical instrument such as intensely shaking forceps and where a bird's-eye view image corresponding to the background shakes, the correction intensity of the blurring correction is reduced to suppress shaking of the bird's eye view, making the observation target such as the living organism easier to observe. Additionally, even in a case where the range imaged by the imaging section is intentionally moved such as a case where the scope of the endoscope apparatus or the like is intentionally moved, the correction intensity of the blurring correction is reduced to suppress correction of image blurring caused by the intentional motion, making the observation target such as the living organism easier to observe.

Additionally, the control apparatus 200 may control the operations related to the correction of image blurring according to the ratio of a region of the subject corresponding to the observation target such as the living organism whose region is shielded, in the screen (in other words, the input image signal), by a subject such as the surgical instrument or the visible gaseous substance that is different from the observation target. By way of a more specific example, the control apparatus 200 may reduce the degree of correction of image blurring with increasing ratio of the region of the subject corresponding to the observation target whose region is shielded by another subject, or disable application of image blurring. With such a configuration, for example, even under circumstances where an increased occupancy of the another subject in the screen makes extraction of feature amounts difficult to reduce the reliability of the correction value for the blurring correction, the observation target such as the living organism can be prevented from becoming difficult to observe by reducing the correction intensity of the blurring correction.

Needless to say, the above-described configuration is only an example and is not intended to limit the contents of the control related to the correction of image blurring performed by the control apparatus 200 according to the present embodiment. As input information, information related to an imaging environment for the observation target such as the living organism can be utilized, the information being, for example, the state of the surgical instrument or motion (vibration) of the bed. Additionally, by way of another example, instead of the zoom magnification, information related to the imaging conditions for the observation target such as the living organism, for example, information related to AF/AE, can be utilized as input information. Additionally, on the basis of the property that image blurring is estimated by extracting feature amounts from the input image signal, a detection result for a factor making extraction of the feature amounts difficult may be utilized as input information. Note that, in this case, the observation target such as the living organism can be prevented from becoming difficult to observe by, for example, reducing the correction intensity of correction of image blurring or temporarily disabling the correction according to the detection result for the factor making extraction of the feature amounts difficult.

The preferred embodiment of the present disclosure have been described in detail with reference to the attached drawings. However, the technical scope of the present disclosure is not limited to such examples. A person with an ordinary skill in the art of the present disclosure may obviously arrive at many varied or modified examples within the range of technical concepts recited in claims, and it is understood that these examples, needless to say, belong to the technical scope of the present disclosure.

Additionally, the effects described herein are only descriptive or illustrative and not restrictive. In other words, in addition to or instead of the above-described effects, the technique according to the present disclosure may produce other effects obvious, from the description herein, to a person with an ordinary skill in the art.

Note that the following configurations also belong to the technical scope of the present disclosure.

(1) A control apparatus including:

an estimating section calculating motion of an entire image on the basis of an image signal corresponding to an optical image of a living organism input from a predetermined imaging section, to estimate blurring of the entire image according to a result of the calculation; and a control section controlling an operation related to correction of the blurring of the entire image by controlling a coefficient for controlling an amount of correction of the blurring on the basis of a zoom magnification of the imaging section such that a degree of correction of the blurring increases consistently with the zoom magnification.

(2) The control apparatus according to (1) described above, in which the control section provides control to suppress correction of the blurring in a case where the zoom magnification is lower than or equal to a threshold.

(3) The control apparatus according to (1) or (2) described above, including:
an extracting section extracting a feature point from the image signal, in which
the estimating section calculates the motion of the entire image on the basis of a result of extraction of the feature point.

(4) A control apparatus including:
an estimating section calculating motion of an entire image on the basis of an image signal corresponding to an optical image of a living organism input from a predetermined imaging section, to estimate blurring of the entire image according to a result of the calculation, and
a control section controlling an operation related to correction of the blurring of the entire image on the basis of a ratio of a region of the living organism in the image signal, the region being shielded by a subject different from the living organism.

(5) The control apparatus according to (4) described above, in which
the control section controls a coefficient for controlling the amount of correction of the blurring according to the ratio of the region.

(6) The control apparatus according to (5) described above, in which
the control section controls the coefficient to reduce a degree of correction of the blurring with an increasing ratio of the region.

(7) The control apparatus according to (4) described above, in which
the control section provides control to suppress correction of the blurring according to the ratio of the region.

(8) The control apparatus according to any one of (4) to (7) described above, in which
the subject includes a surgical instrument.

(9) The control apparatus according to any one of (4) to (7) described above, in which
the subject includes a visible gaseous substance.

(10) The control apparatus according to any one of (4) to (9) described above, in which
the ratio of the region is calculated according to a recognition result for the subject.

(11) The control apparatus according to any one of (4) to (10) described above, including:
an extracting section extracting a feature point from the image signal, in which
the estimating section calculates the motion of the entire image on the basis of a result of extraction of the feature point.

(12) A control method including:
calculating, by a computer, motion of an entire image on the basis of an image signal corresponding to an optical image of a living organism input from a predetermined imaging section, to estimate blurring of the entire image according to a result of the calculation; and
controlling, by the computer, an operation related to correction of the blurring of the entire image by controlling a coefficient for controlling an amount of correction of the blurring on the basis of a zoom magnification of the imaging section such that a degree of correction of the blurring increases consistently with the zoom magnification.

(13) A control method including:
calculating, by a computer, motion of an entire image on the basis of an image signal corresponding to an optical image of a living organism input from a predetermined imaging section, to estimate blurring of the entire image according to a result of the calculation, and
controlling, by the computer, an operation related to correction of the blurring of the entire image on the basis of a ratio of a region of the living organism in the image signal, the region being shielded by a subject different from the living organism.

(14) A program causing a computer to execute:
calculating motion of an entire image on the basis of an image signal corresponding to an optical image of a living organism input from a predetermined imaging section, to estimate blurring of the entire image according to a result of the calculation; and
controlling an operation related to correction of the blurring of the entire image by controlling a coefficient for controlling an amount of correction of the blurring on the basis of a zoom magnification of the imaging section such that a degree of correction of the blurring increases consistently with the zoom magnification.

(15) A program causing a computer to execute:
calculating motion of an entire image on the basis of an image signal corresponding to an optical image of a living organism input from an imaging section of a medical observation apparatus, to estimate blurring of the entire image according to a result of the calculation; and
controlling an operation related to correction of the blurring of the entire image on the basis of a ratio of a region of the living organism in the image signal, the region being shielded by a subject different from the living organism.

REFERENCE SIGNS LIST

100 Endoscopic surgery system
101 Endoscope
117 Surgical instrument
127 Support arm apparatus
139 Camera control unit
141 Display apparatus
143 Light source apparatus
145 Arm control apparatus
147 Input apparatus
149 Treatment instrument control apparatus
151 Insufflation apparatus
153 Recorder
155 Printer
200 Control apparatus
210 Image processing unit
211 First control section
215 Estimating section
217 Second control section
219 Correction processing section
250 Determining section

The invention claimed is:
1. A control apparatus, comprising:
circuitry configured to:
calculate motion of an entire image based on an image signal corresponding to an optical image of a living organism, wherein the image signal is received from an imaging section of a medical observation apparatus;
estimate blurring of the entire image based on the calculation of the motion;
determine an increase in occupancy of a subject different from the living organism in the image signal;
determine an increase in a ratio of a region of the living organism that is shielded by the subject in the image signal, wherein the increase in the ratio is determined based on the increase in the occupancy of the subject; and control an operation to reduce a degree of correction of the blurring of the entire image based on the determined increase in the ratio of the region of the living organism shielded by the subject in the image signal.

2. The control apparatus according to claim 1, wherein the circuitry is further configured to control a coefficient for the reduction of the degree of the correction of the blurring according to the ratio of the region.

3. The control apparatus according to claim 1, wherein the circuitry is further configured to suppress the correction of the blurring according to the ratio of the region.

4. The control apparatus according to claim 1, wherein the subject includes a surgical instrument.

5. The control apparatus according to claim 1, wherein the subject that shields the region of the living organism includes a visible gaseous substance.

6. The control apparatus according to claim 1, wherein the circuitry is further configured to calculate the ratio of the region based on a recognition result of the subject.

7. The control apparatus according to claim 1, wherein the circuitry is further configured to:
   extract a feature point from the image signal; and
   calculate the motion of the entire image based on the extraction of the feature point.

8. A control method, comprising:
   calculating, by a computer, motion of an entire image based on an image signal corresponding to an optical image of a living organism, wherein the image signal is received from an imaging section of a medical observation apparatus;
   estimating, by the computer, blurring of the entire image based on the calculation of the motion;
   determining, by the computer, an increase in occupancy of a subject different from the living organism in the image signal;
   determining, by the computer, an increase in a ratio of a region of the living organism that is shielded by the subject in the image signal, wherein the increase in the ratio is determined based on the increase in the occupancy of the subject; and
   controlling, by the computer, an operation to reduce a degree of correction of the blurring of the entire image based on the determined increase in the ratio of the region of the living organism shielded by the subject in the image signal.

9. A non-transitory computer-readable medium having stored thereon, computer-executable instructions which, when executed by a computer, cause the computer to execute operations, the operations comprising:
   calculating motion of an entire image based on an image signal corresponding to an optical image of a living organism, wherein the image signal is received from an imaging section of a medical observation apparatus;
   estimating blurring of the entire image based on the calculation of the motion;
   determining an increase in occupancy of a subject different from the living organism in the image signal;
   determining an increase in a ratio of a region of the living organism that is shielded by the subject in the image signal, wherein the increase in the ratio is determined based on the increase in the occupancy of the subject; and
   controlling an operation to reduce a degree of correction of the blurring of the entire image based on the determined increase in the ratio of the region of the living organism shielded by the subject in the image signal.

* * * * *